United States Patent
Cruz Morales et al.

(10) Patent No.: US 10,414,796 B2
(45) Date of Patent: Sep. 17, 2019

(54) GENETIC SYSTEM FOR PRODUCING A PROTEASES INHIBITOR OF A SMALL PEPTIDE ALDEHYDE TYPE

(71) Applicant: Centro de Investigación y de Estudios Avanzados del Instituto Politécnico Nacional, Ciudad de México, CDMX (MX)

(72) Inventors: Pablo Cruz Morales, Guanajuato (MX); Francisco Barona Gómez, Guanajuato (MX); Hilda Eréndira Ramos Aboites, Guanajuato (MX)

(73) Assignee: Centro de Investigación y de Estudios Avanzados del Instituto Politécnico Nacional, Mexico City (MX)

( * ) Notice: Subject to any disclaimer, the term of this patent is extended or adjusted under 35 U.S.C. 154(b) by 41 days.

(21) Appl. No.: 15/537,125

(22) PCT Filed: Dec. 14, 2015

(86) PCT No.: PCT/IB2015/059566
§ 371 (c)(1),
(2) Date: Jun. 16, 2017

(87) PCT Pub. No.: WO2016/097957
PCT Pub. Date: Jun. 23, 2016

(65) Prior Publication Data
US 2018/0265545 A1 Sep. 20, 2018

(30) Foreign Application Priority Data
Dec. 16, 2014 (MX) .................. MX/a/2014/015560

(51) Int. Cl.
*C12N 15/70* (2006.01)
*C07K 5/065* (2006.01)
*C07C 279/12* (2006.01)
*C12N 15/63* (2006.01)

(52) U.S. Cl.
CPC ........ *C07K 5/06078* (2013.01); *C07C 279/12* (2013.01); *C12N 15/635* (2013.01); *C12N 15/70* (2013.01)

(58) Field of Classification Search
CPC ... C07K 5/06078; C12N 15/635; C12N 15/70
See application file for complete search history.

(56) References Cited

FOREIGN PATENT DOCUMENTS

WO 99/67374 A1 12/1999

OTHER PUBLICATIONS

International Search Report and Written Opinion dated Jun. 6, 2016 issued in PCT/IB2015/059566.
Cruz-Morales, P. et al. "The genome sequence of Streptomyces lividans 66 reveals a novel tRNA-dependent peptide biosynthetic system within a metal-related genomic island", Genome Biology and Evolution, 2013, pp. 1165-1175, vol. 5, No. 6. (11 pages).
Gomez-Escribano, J.P . et al. "Heterologous expression of natural product biosynthetic gene clusters in Streptomyces coelicolor: from genome mining to manipulation of biosynthetic pathways", Journal of Industrial Microbiology & Biotechnology, 2014, pp. 425-431, vol. 41, No. 2. (7 pages).
Licona-Cassani, C. et al. "Systems Biology Approaches to Understand Natural Products Biosynthesis", Frontiers in Bioengineering and Biotechnology, 2015, vol. 3, article 199. (8 pages).
Kisselev, A.F. et al. "Proteasome inhibitors: an expanding army attacking a unique target", Chemistry & Biology, 2012, pp. 99-115, vol. 19, No. 1. (29 pages).
Chen, Y. et al.: "Proteomics guided discovery of flavopeptins: anti-proliferative aldehydes synthesized by a reductase domain-containing non-ribosomal peptide synthetase", J. Am. Chem. Soc., 2013, pp. 10449-10456, vol. 135, No. 28. (16 pages).

*Primary Examiner* — Karen Cochrane Carlson
(74) *Attorney, Agent, or Firm* — Rothwell, Figg, Ernst & Manbeck, P.C.

(57) ABSTRACT

The present invention describes a new peptide aldehyde produced naturally by *Streptomyces lividans* 66, which we have called livipeptin. Using genome mining of natural products, we predicted that SLI0883-5 genes encode an unprecedented biosynthetic system, unusually small (4.6 Kbp), which produces an acylated peptide aldehyde. Because of the chemical characteristics of the predicted compound, we postulated its anti-proteolytic activity, which we confirmed by identifying and purifying this compound through metabolic profiles of HPLC and MS of the mutated strain lacking these three genes and the wild strain. To this objective, we identified the conditions wherein these genes are strongly expressed. The livipeptin was purified and its inhibitory activity on the proteolytic activity of selected proteases was demonstrated in vitro. The design of an expression cassette for its heterologous expression is also described plus its use for heterologous protein production.

14 Claims, 9 Drawing Sheets

Specification includes a Sequence Listing.

Figure 1

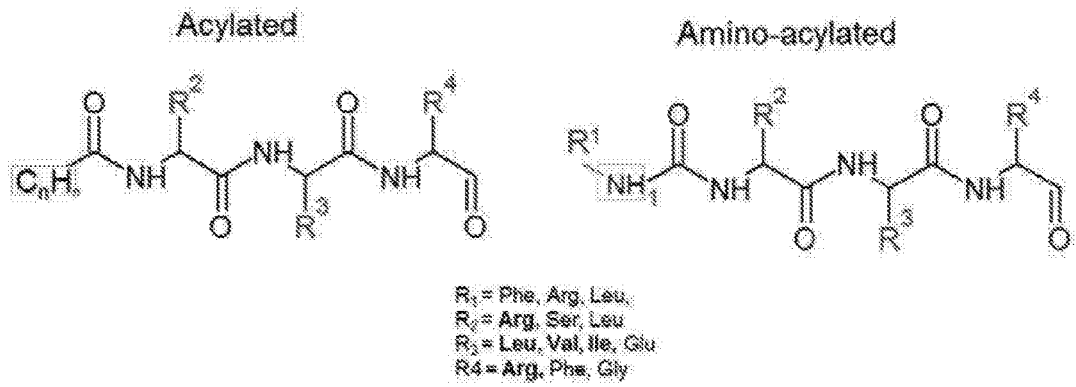

Figure 6

| Gene | Predicted Function |
|---|---|
| SLI0883 | Non-ribosomal peptide synthetase |
| SLI0884 | Leucyl/Phenylalanyl-tRNA-protein transferase |
| SLI0885 | N-Acetyltransferase |
| SLI0886 | O-methyltransferase, family 2 |
| SLI0887 | Butyryl-CoA dehydrogenase |
| SLI0888 | TenA family transcriptional regulator |
| SLI0889 | Major facilitator superfamily MFS1 |
| SLI0890 | Putative cytochrome P450 monooxygenase |
| SLI0891 | Pyridoxamine 5'-phosphate oxidase-related, FMN-binding |
| SLI0892 | Unknown |
| SLI0893 | CsoR-like DUF156 |
| SLI0894 | Heavy metal-associated domain-containing secreted protein |

Figure 2

| SPA | Producer Strain | Target | Protease class | Reference |
|---|---|---|---|---|
| Antipain | *Streptomyces yokosukanensis* MC829-AS1, *Streptomyces mauvecolor* | Trypsin, plasmin, papain | Cystein y Serine-(Thiol proteases | Suda et al, 1972; Umezawa et al, 1972, |
| Chimostatin | *Streptomyces hygroscopicus* MC521-C8, *Streptomyces lavendulae* MC524-C1 | ChimoTrypsin, Papain | Cystein y Serine-(Thiol proteases | Umezawa et al, 1970; Tatsuta et al, 1973, |
| Leupeptins | *Streptomyces roseus* MA839-A1 | Trypsin, plasmin, Papain, 20s proteosome subunit | Serine/Cystein/threonine proteases | Aoyagi et al, 1969 |
| Elastatinal | *Streptomyces griseoruber* MD 469-CG8 | Elastase | Serine-proteases | Umezawa et al, 1973, Okura et al, 1975 |
| Pepstatin | *Streptomyces testaceus* Hamada et Okami, *Streptomyces argenteolus* var. Toyonakensis | Pepsina, gastricsina cathepsina D y renina | Aspartatil-proteases | Umezawa et al, 1970, Morishima et al, 1970 |
| MAPI's | *Streptomyces nigrescens* WT-27 | Subtilisin | Alkaline proteases | Murao y Watanabe, 1977; Watanabe et al, 1979 (alpha) & 1982 (Beta) |
| Flavopeptin | *Streptomyces* sp. NRRL-F6652, *Streptomyces f lavogriseus* ATCC 33331 | Papain, calpain | Cystein-proteases | Chen et al, 2013 |
| Nerfilin | *Streptomyces halstedii* 2723-SV2 | Cathepsina, Papain | Cystein-proteases | Hirao et al, 1995 |
| Staccopins | *Staphylococcus tanabeensis* | Calpain, Papain | Cystein-proteases | Saito et al, 1987 |
| Strepin | *Streptomyces tanabeensis* (SAB-934) | Trypsin, Papain, calpain | Cystein y Serine-(Thiol proteases | Ogura et al, 1985 |
| Tyropeptins | *Kitasatospora* sp. MK993-dF2 | 20s proteosome subunit | Treonin-proteases | Momose et al, 2001 (a &b) |
| Tyrostatin | *Kitasatospora* sp. Cepa 55 | Papain, Ficain y carboxyl-proteinases | Carboxyl-proteinases/ Cystein-proteases | Oda et al, 1989 |
| Bacithrocins | *Bacillus laterosporus* Laubach NR2988 | Trombin, Factor Xa, Trypsin y Papain | Serine-proteases/Tiol proteases | Kamiyama et al 1994 |
| Thiolstatin | *Bacillus cereus* EY-21 | Papain, Trypsin | Cystein y Serine-(Thiol proteases | Murao et al, 1985 |
| Acetyl-Leu-arginal or Caricastatin | Unnidentified strain BMG520-yF2 y *Nigrosabulum* novosp. | Dipeptidyl aminopeptidase III, Papain, Ficain, Bromelin | Cystein y Serine-(Thiol proteases | Nishikiori et al, 1984; Murao et al, 1987 |
| Fellutamides | *Penicillum fellutanum* | 20s proteosome subunit | Threonyl-proteases | Shigemori et al, 1991 |
| GE20372 | *Streptomyces* sp. ATCC 55925 | HIV-1 aspartyl-protease | Aspartyl-proteasee | Stefanelli et al, 1995 |
| Nostosins | *Nostoc* sp. cepa FSN | Trypsin | Seryl-proteases | Liu et al 2014 |

Figure 10

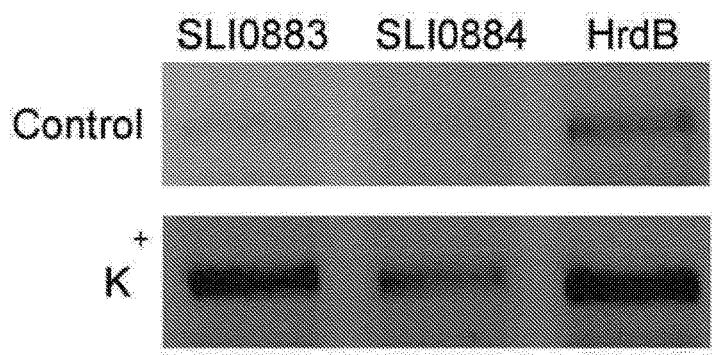

SLI0883: Adenylation (A) Peptidyl carrier protein (PCP) and reductase(R) domains
SLI0884: Leucyl-Phenilalanyl-tRNA-protein transferase
SLI0885: N-acyl trasferase

GENETIC SYSTEM FOR PRODUCING A PROTEASES INHIBITOR OF A SMALL PEPTIDE ALDEHYDE TYPE

CROSS-REFERENCE TO RELATED APPLICATIONS

The present is a national stage filing under 35 U.S.C. § 371 of PCT/IB2015/059566, filed on 14 Dec. 2015, and claims the benefit of priority to Mexican Application No. MX/a/2014/015560, filed on 16 Dec. 2014. Each application is incorporated herein by reference in its entirety.

The present application includes a Sequence Listing filed in electronic format. The Sequence Listing is entitled "4604-102_ST25.txt" created on Dec. 21, 2018, and is 12,981 bytes in size. The information in the electronic format of the Sequence Listing is part of the present application and is incorporated herein by reference in its entirety.

FIELD OF THE INVENTION

The present invention relates to the field of genetic engineering and more particularly, to the isolation, characterization and production of secondary metabolites or natural products (NP) characterized by being small peptide aldehydes (SPA) with protease inhibitory activity, and to the genetic system for its production in prokaryotes or eukaryotes; it also refers to the biosynthetic pathway and the chemical diversity derived by genetic engineering methods or the modification of growing conditions.

BACKGROUND OF THE INVENTION

The term natural product (NP) or secondary metabolite refers a group of various low molecular weight compounds produced by a microorganism whose production is not always essential, but is surely essential for the adaptation and survival thereof. This implies that the metabolites are not preserved and may even be specific to a single strain of bacterial specie. It also means that these compounds are produced under certain conditions, which tend to differ from laboratory conditions. The most common NP belong to the following categories: i) terpenoids and steroids (e.g. taxol); ii) alkaloids (eg. morphine; iii) substances derived from fatty acids (eg. prostaglandin $E_1$, which is an eicosanoid), and polyketides (eg. erythromycin); iv) non-ribosomal peptides (such as penicillin), or small peptides aldehydes (such as leupeptin); and v) enzyme cofactors (such as cobalamin).

It has been established that the genes responsible for the synthesis of natural products in bacteria are grouped in discrete regions of their chromosomes, which implies that its regulation is mediated in a fine way to match the presence of suitable precursors and enzymes involved in a concerted way for the accelerated production of these compounds.

The genome mining of natural products is a strategy used in microbiology for the analysis of microbial genomes in order to predict their ability to produce new chemical compounds [1]. In addition, the use of genome mining tools helps establish the logical biosynthetic which occurs on the enzymatic transformations of the pathway, as well as predicts substrates and products in the case of uncharacterized microbial enzymes. This knowledge allows the use of genetic engineering methods of microorganisms for producing natural products efficiently and cost-effectively. This helps also to create strategies or methods to select and define the efficiency of metabolites, evaluate their activity against pathogens, explore ways to modify these metabolites to improve their efficiency, and elucidate whether the bioactivities of these metabolites have some relevance to medicine or industry [2].

Using these strategies, success is ultimately aimed at finding new types of drugs such as antibiotics, also to improve production methods and synthesis, and better ways to examine the effectiveness of antibiotics in humans, plants, and animals.

Once the genes that direct the synthesis of promising molecules are identified by genome mining, molecular biology techniques are used to establish the relationship between the production of the corresponding molecule and the biosynthetic genes. In the organism that synthesizes, it done through the comparative analysis of the metabolomes of mutant lacking genes essential for the production of molecules and the wild strain. The relationship gene-metabolite also can be established through the cloning of biosynthetic genes and their introduction in a host for heterologous production. The objective of these strategies is focused on discovering new types of molecules of pharmacological interest such as antibiotics, or inhibitors and pigments that can also be used in the industry, also to improve production methods and synthesis of known products and to improve the efficacy of drugs by searching their variants for use on humans, plants and animals.

The bacteria that most have been used for the production of NP's are species of the genus *Streptomyces*, Gram-positive bacteria, belonging to the family of actinobacterium, whose genomes have a content of 72% of G+C on average. The *Streptomyces* have been isolated from different habitats, manly from all types of soil and marine sediment. Most of them are free living saprophytes and they degrade organic matter of their habitats competing with a large number of species, so it is believed to they have evolved to produce a wide range of natural products for their survival [3].

Between the NPs produced by members of the genus *Streptomyces* are small peptide aldehydes (SPA), examples of them are leupeptin, antipain, and chymostatin, which are the protease inhibitors more used in industry and biotechnological research. Inhibiting protease enzymes, which are responsible for the degradation of peptides and exogenous or endogenous proteins, is vital for many biological functions. Therefore, proteases are considered promising targets for the development of therapies for treatment diseases where proteolysis is relevant; for example, diseases associated with defects in the functioning of proteasome, a protein complex responsible for degrading endogenous proteins; calpains, hyperactive proteases in conditions such as Alzheimer disease and cataract formation; and cathepsins, which have been linked to cancer and inflammatory diseases [4-6].

Proteases are also vitally important for various pathogenic agents during infectious processes, so it has explored the use of protease inhibitors to combat the human immunodeficiency virus, cytomegalovirus, among others [7-8]. In this context, the protease inhibitors, including those belonging to the large family of small peptide aldehyde, such as leupeptin (which has been called here SPAs) are being studied extensively for its development as therapeutic agents [4-6]. Moreover, aside from their potential therapeutic use, SPAs are widely used in industry and research laboratories for protein purification processes, wherein proteolysis is a counterproductive process that needs to be inhibited. The industry and the research and diagnostic laboratories are the most important market for these compounds, being leupeptin and antipain the most used. Practically all the processes of production of heterologous proteins, some of them with the highest value added such as next generation vaccines, involve the use of protease inhibitors like leupeptin or one of its derivatives. Therefore, these molecules are marketed both in bulk and in pure versions and are obtained through bacterial fermentation of the genus *Streptomyces*, being these the most widely used and more valuable products than the few synthetic variants able to be obtained.

The first natural products with anti-proteolytic activity belonging to this family were discovered in the late sixties of the last century, in fermentation extracts of bacteria of the genus *Streptomyces*. Their discovery was the result of traditional screening methods or screening for activity followed by isolation, purification and chemical characterization. The compounds belonging to this family have also been detected in other members of actinobacteria and other Gram positive bacteria of the genera *Bacillus* and *Staphylococcus*, cyanobacteria and fungi of the Ascomycota group.

Beside their peptide nature and low molecular weight, which ranges between 300 and 900 Daltons, SPAs share other chemical characteristics such as: (i) lack of N-terminal groups, because they are "protected" with acyl groups of one or more carbons, with ureido-amino acid groups leading to an acylated or aminoacylated end, which has a terminal carboxyl group; and (ii) the presence of a terminal aldehyde group derived from the modification of the carboxyl terminus of the peptide chain by a reductive process, which is responsible for the biological activity of the molecule. The aldehyde end interacts with the active sites of proteases forming hemiacetals or hemithioacetals with catalytic residues, often serins or cysteines, disrupting their functioning (FIG. 1) [5,9-11].

From this general structure, SPAs can be divided into two sub-classes, considering the characteristics of their functional groups: (i) those with a terminal group protected by an acyl group; e.g., flavopeptin, tyrostatin, tyropeptin, nerfilin, strepin, leupeptin, bacithrocin, thiolstatin and acetyl-leucine-arginal; and (ii) those wherein the N-terminal joins an ureido motive, which in turn is attached to an amino acid via an amidic bond; e.g., quimostatin (or chymostatin), MAPI, GE20372, antipain and elastatinal. This setting allows to alter the order of the peptide chain, where the ureido group acts as an adapter changing the order of the peptide, from N-terminal to C-terminal through C-terminal to C-terminal, resulting in peptides with chemical and biological characteristics different from traditional ribosomal peptides.

The size of the peptide chain may range from two to six residues, while the acyl groups may be from two up to nine carbon atoms, as shown in FIG. 3. Based on SPAs whose structures have been determined, the residues or amino acids arginine, phenylalanine, tyrosine, leucine, isoleucine, valine and glutamine are recognized forming peptide chains. In most SPAs, the aldehyde group is derived from the carboxylic group of phenylalanine, tyrosine or arginine, while the next amino acid is typically any of the branched-chain group, either isoleucine, leucine or valine.

Outside this classification, some exceptions have been reported for example, elastatin, which consists of isovaleryl-ureido-arginine-glutamine-alanilal, and two of the smaller SPAs that are known to date: bacitrocins and thiolstatin, both inhibitors of cysteine/serine proteases produced by bacteria of the genus *Bacillus*. These peptides, which are smaller than the commonly found in SPAs, are formed by acyl-phenylalanine-arginal groups [12-13].

Regarding the biosynthesis of SPAs, since the discovery of leupeptin in 1969 [14-15], a number of studies have described the isolation of new SPAs and the taxonomic identification of the microorganisms that produce them, their fermentation and purification methods, chemical structures and biological activity (FIG. 2). However, despite the enormous importance of these compounds, little is known of their biosynthesis, including the compounds with a broad market, such as antipain, quimostatin and leupeptin.

Early efforts to characterize the biosynthesis of leupeptin were based on the fractionation and purification of protein extracts of *Streptomyces roseus*, the producing organism of leupeptin, and the use of these extracts for enzyme assays in vitro. These studies suggested that a non-ribosomal peptide synthase (NRPS) and a reductase would be involved in the pathway synthesis of this compound. These studies determined the incorporation of L-Leucine, D-Leucine, and acetyl-CoA as precursors [16]. Recently, the synthesis pathway of flavopeptin has been described, an aldehyde peptide with protease inhibitory activity [17]. Flavopeptin is synthesized by a NRPS whose domains are organized according to the order in which the precursors are incorporated into the final structure; i.e., it is colinear. Synthetase flavopeptin includes a transference domain of acyl groups, which is responsible for the incorporation of the acylation of the sixth amino acid of the peptide (N-acyl terminal). The synthase also includes adenylation domains, carrying proteins of peptidiles and condensation domains for the successive incorporation of six precursor amino acids, Ile-Gln-Ile-Gln-Val/Ile-Phe, (SEQ ID NO: 8 and SEQ ID NO: 9) an epimerization domain that acts on the fourth residue (Gln) and finally a reductase domain, which catalyzes the last step of the pathway consisting in releasing the nascent peptide from the synthase by reducing the terminal carboxylic group, which results in the formation of the characteristic aldehydic group (FIG. 4).

As already mentioned, most of the protease inhibitors on the market are natural products of microbial origin. Generally, the use of these compounds to prevent proteolysis consists in their addition during the protein extraction process, which implies that the compound should be fermented and purified for later use. Furthermore, it is known that the products obtained by fermentation are usually mixtures of related molecular species, and they show improved biological efficiency compared with 100% pure synthetic products, which is reflected in the higher cost of fermentation products.

An economically favorable alternative for the realization of this alternative process is the production of protease inhibitors simultaneously to the production of value-added proteins through the heterologous expression of the biosynthetic pathway of a protease inhibitor in an organism, which in turn produces the protein of interest. However, this has not been reported to date, most likely because of the lack of knowledge of the genetic bases that direct the synthesis of most SPAs and the difficulties encountered in the heterologous expression of NRPs encoded in large genetic regions (>20 Kbp judging by the chemical structure of three or more amino acids). To develop a system with these characteristics it is therefore necessary to know the genetic basis of the biosynthesis inhibitor to be expressed and the construction of genetic systems that allow the heterologous expression in a controlled manner of said genes into the cell line used for biotechnological purposes.

From the above, the following main problems are derived that hinder the development of these expression systems: (i) the almost total lack of knowledge of the genetic basis of the biosynthesis of protease inhibitors of the SPAs-type, including leupeptin, antipain and quimostatin; and (ii) based on the historic biochemical studies and the recent report of flavopeptin, it is expected that the synthases, which could direct their synthesis, involve complex biosynthetic systems coded by large genetic regions (>20 Kb): said genetic systems could hardly be expressed heterologously with efficiency in the cell lines used by the industry to produce high-value proteins.

Among the patents that relate to the obtainment and uses of SPAs having market value, the European patent EP1318198 describes a process for producing a recombinant peptide, which involves the addition of an inhibitor of chymotrypsin to the culture medium. The patent U.S. Pat. No. 4,066,507 describes a process for producing L-leupeptins, while the patent US20110183915 relates to treatments against cancer cells using a small molecule (leupeptin) to cause necrosis in them, but does not affect normal cells. As can be seen, because of its high value and potential, it is necessary to continue with the determination of the genetic bases and biosynthetic mechanisms involved in the production of SPAs.

BRIEF DESCRIPTION OF THE INVENTION

The present invention relates to the isolation and characterization of a new peptide aldehyde SPA type, which we call livipeptin produced by *Streptomyces lividans* 66, using genome mining of NPs, both traditional and mediated by evolutionary principles (EvoMining). We determined that livipeptin has protease inhibitory activity, its effect in the heterologous production of proteins, and the genetic basis for their biosynthesis. We also use synthetic biology for the heterologous expression of the biosynthetic genes and the production of various compounds with the functional groups of the native product, livipeptin, with inhibitory activity on various proteases.

BRIEF DESCRIPTION OF THE FIGURES

FIG. 1. Shows that SPAs have aldehyde terminal and acyl or amino acylated groups. The aldehyde group is essential for the inhibitory activity of the compounds.

FIG. 2. Shows some SPAs and their characteristics.

FIG. 6. Shows the function prediction of the biosynthetic genes cluster of NRPS-tRNA of *S. lividans* 66.

FIG. 10. Shows the transcriptional response of *S. lividans* 66 to potassium. *S. lividans* 66 was inoculated in liquid medium and after 66 hours of incubation, it was added to KCl cultures. After 4 hours of the addition of the metals, total RNA was extracted and subjected to RT-PCR analysis. HrdB is a preserved housekeeping sigma factor, which was used as a control.

DETAILED DESCRIPTION OF THE INVENTION

Figure 3:
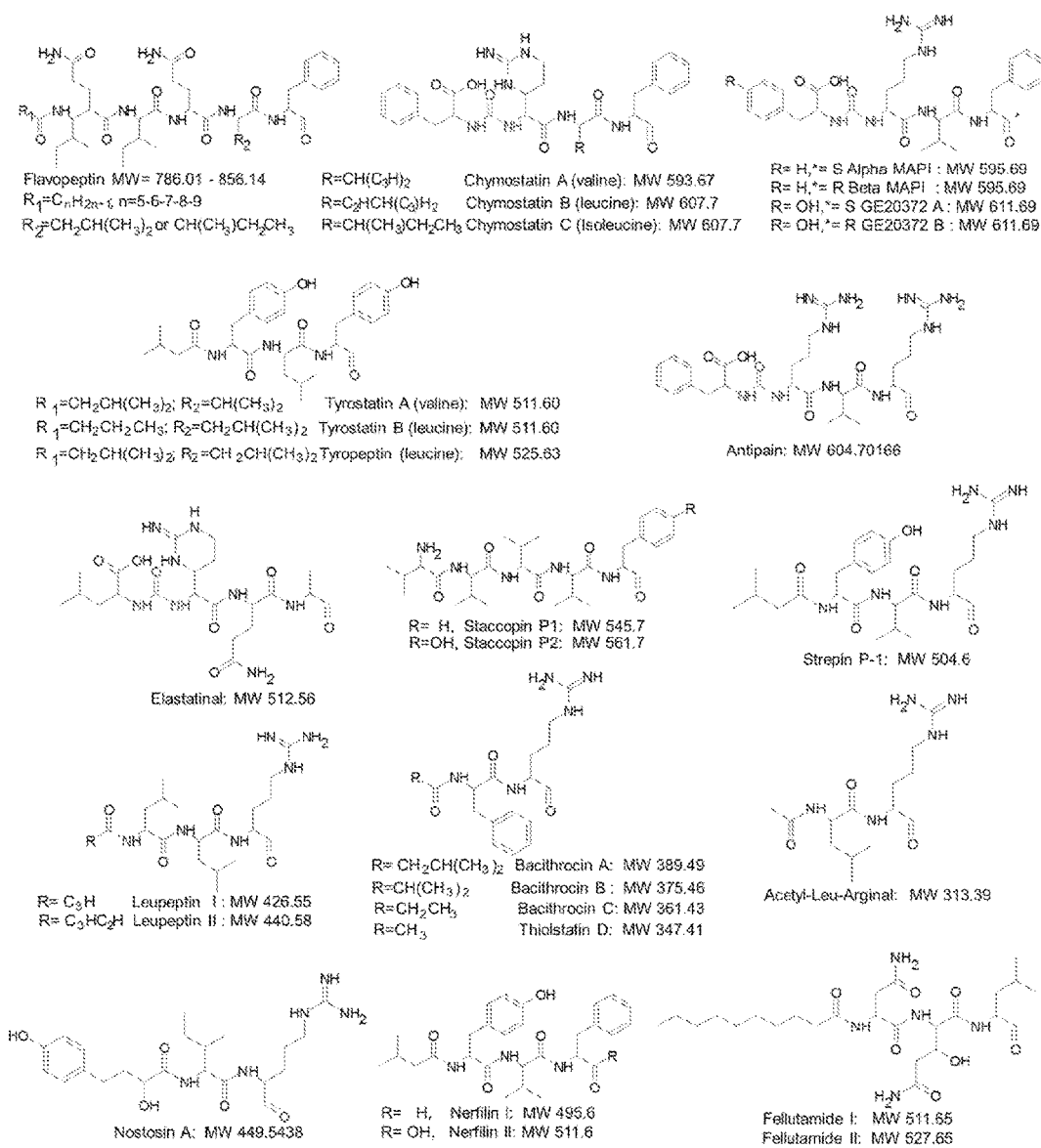
FIG. 3. Shows the chemical structures and theoretical masses of known SPAs. The aldehyde groups are marked with *, while the groups that protect the N terminal group are marked with **.
Figure 4:
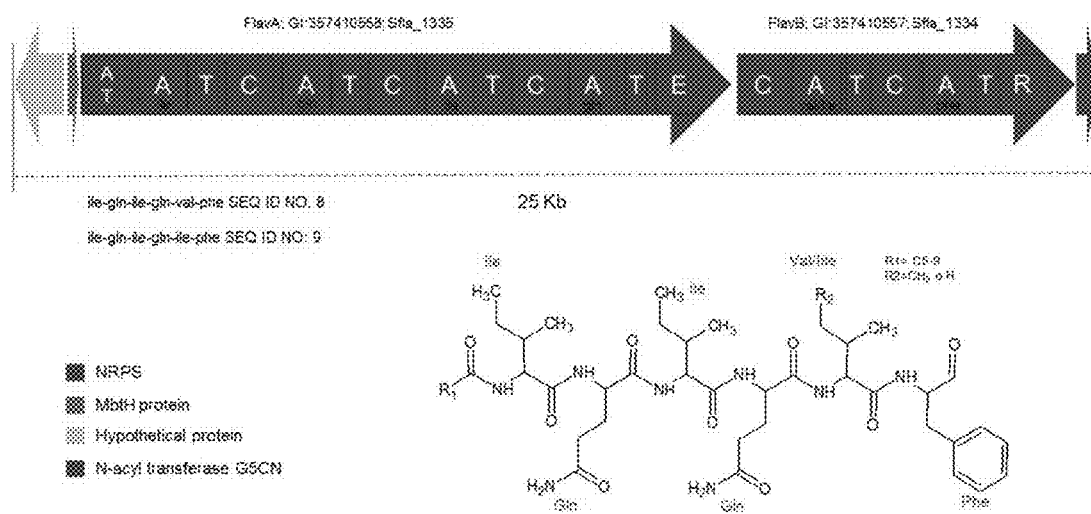
FIG. 4. Shows the organization of the NRPs of flavopeptin and its chemical structure.

The present invention originally comes from a study on the evolution of the metabolic repertoire of Streptomyces, which was based on the development of a strategy that combines genome mining and evolutionary theory resulting in a bioinformatic method, which is different from those known in the prior art (AntiSMASH [18]) that facilitates the discovery of new biosynthetic pathways of NPs from genomic sequences of actinobacteria. This bioinformatic method called EvoMining for the purposes of this invention, was developed from a functional and comparative genomic perspective, making the integration of the NPs gene clusters database and thus conduct a genome mining emphasizing evolutionary concepts, being this bioinformatics application subject of another patent application (MX/a/2015/007200). The present invention arose from genome mining using EvoMining application and led to the determination of a new system for the formation of peptide bonds as explained in detail below.

Postulation of a hybrid biosynthetic pathway (dependent from a tRNA-NRPS association) for peptide bond formation in S. lividans 66. In a previous work, we have reported the genes of a new biosynthetic system of peptide bonds that includes dependent enzymes of aminoacyl-tRNAs within the genome of Streptomyces lividans 66, however was not reported its production, identity, bioactivity or heterologous expression. This system includes an adenylation domain, a carrier protein of peptidiles, and a reductase domain (SLI0883) plus a leucyl-phenylalanyl-tRNA transferase (coding by SLI0884 gen). These enzymes are specifically encoded into SLP3 plasmid, a mobile genetic element functionally linked to the metabolism of metals and metalloids [19].

S. lividans 66 is a strain closely related with S. coelicolor, a model organism of which most of the natural products encoded by its genome have been reported during the first efforts of genome mining [20-21]. These predictions include several pathways and metabolites whose structures have been elucidated. Due that between the genomes of S. lividans 66 and S. coelicolor exists high sequence identity (>95%) is expected that S. lividans 66 produce the same natural products, except for those regions of the genome that are unique for each organism.

The use of EvoMining in the genome of S. lividans 66 led to the prediction of a new biosynthetic pathway encoded in a region of the genome of S. lividans 66 which is absent in S. coelicolor and includes a divergent member of the enzyme family L/F-tRNA-protein transferases (LFT; Enzyme Commission 2.3.2.6) (or tRNA Leucil-phenilalanyl transferase protein) encoded in SLI0884. This enzyme family is implicated in the proteolytic pathway of the so-called N-terminal rule [22-23], and they catalyze the transfer of leucine or phenylalanine of a charged aminoacyl-tRNA, to a basic N-terminal residue of a protein, generally an arginine or lysine through the N-terminal proteins degradation rule [22-23]. It has been postulated previously the recruitment of LFTs for the biosynthesis of NP [24]. The postulation of this enzyme as an interesting catalyst for the biosynthesis of NPs is based on recent findings of peptide tRNA synthases dependent on other families of enzymes in the context of the biosynthesis of NP. Therefore their identification through the use of EvoMining led to the postulation of the presence of a new biosynthetic pathway of NPs of peptidic nature comprising SLI0884 and genes around it.

Another widely used method of genome mining is anti-SMASH [18], which is based on the identification of sequence signatures associated with enzymes from natural products. AntiSMASH coincided with EvoMining to identify a biosynthetic gene cluster based on NRPS in the region wherein recruited LFT (SLI0884) is encoded, according to this prediction the cluster of genes includes 30 genes of which 21 are classified as other genes, including LFT itself (SLI0884). Only 9 of these genes are annotated as biosynthetic genes. This analysis served to corroborate and reinforce the prediction by EvoMining.

Figure 5:
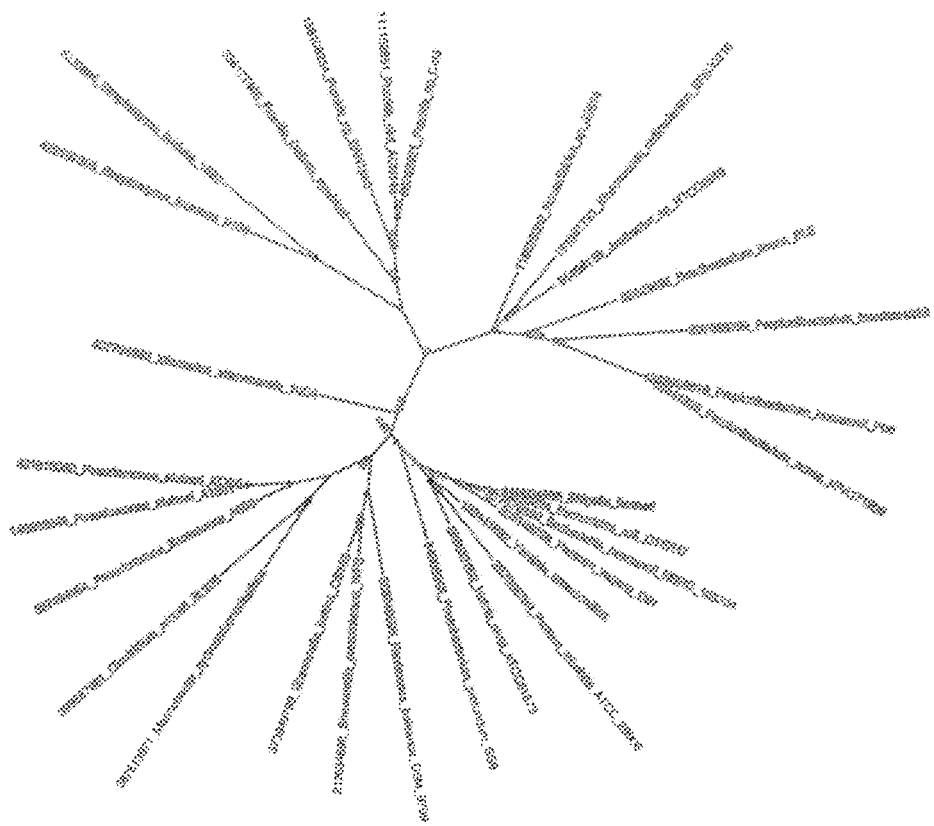
FIG. 5. Shows the phylogenetic reconstruction of the enzyme family L/F-tRNA or LFT. The tree was constructed using MrBayes, wherein the posterior probabilities are shown in the nodes. The actinobacterial members of the LFT enzyme family are shown in branches with *; the LFTs of *Streptomyces* are shown with **. The access number of each family member is indicated before the name of each organism.

Subsequently we performed a phylogenomic analysis of the LFTs enzymes family in actinobacteria. 13 members of the LFT enzymes family within a database of actinobacterial genomes were identified through analysis by EvoMining. Among them, only 2 strains of Streptomyces, S. ipomoea and S. lividans 66 have homologous of LFT. The branches of these enzymes form a single Glade with the longest branch of the phylogeny, indicating a different rate of evolution of other family members (FIG. 5).

Figure 7:
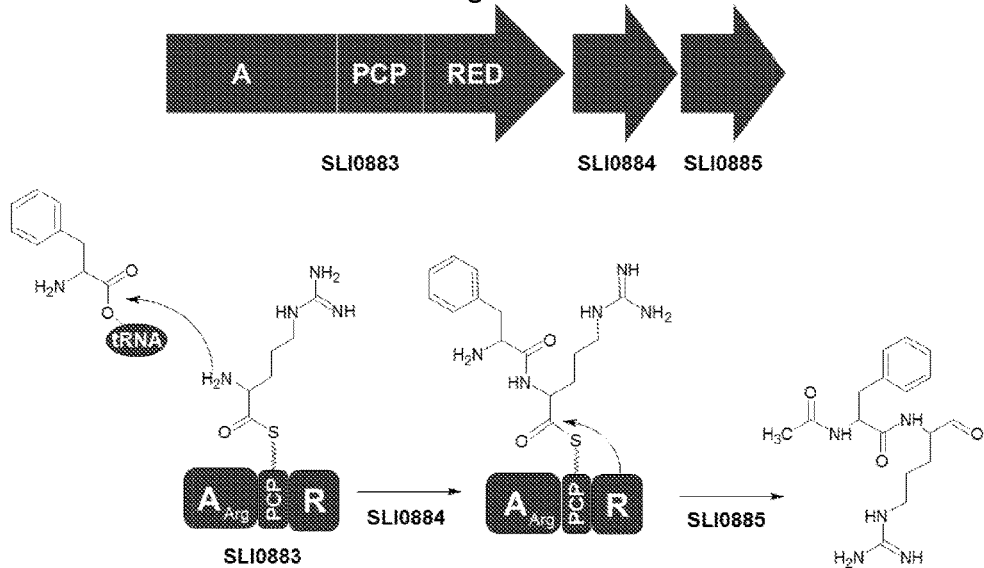
FIG. 7. Shows the prediction of a biosynthetic pathway for a peptide aldehyde (Livipeptin) produced by *Streptomyces lividans* 66. A mechanism of formation of a peptide bond is proposed by a hybrid NRPS-tRNA biosynthesis system. The biosynthetic pathway predicted includes SLI0883: protein includes an adenylation domain, SLI0884: transferase Leucil/Phenylalanyl-tRNA protein and SLI0885: N-acetyl transferase.

The LFT of S. lividans (SLI 0884) is within SLP3, which is a mobile genetic element inserted into the chromosome [19] and shares 35% sequence identity at amino acid level with Aat enzyme (LFT of E. coli, GenBank locus_tag=ECK0876). SLI0884 is located downstream of an unusual gene encoding a protein similar to NRPS that contains only one adenylation domain (A) without a condensation domain (C) nor of thioesterase (TE), but does contain a reductase domain (R). The lacking domains, canonicals of a NRPS, are neither found in the vicinity of this genomic locus. The surroundings of the encoding region of this NRPS are conserved in S. ipomoea, including the homologous of the LFT (GenBank Accession: ZP_19189297). The closest homologous outside Streptomyces were found in the species of the genus Frankia; however, their genetic context is not related to any NRPS nor to any NPs biosynthetic enzyme; so, one might assume a proteolytic paper. Also, a similar scenario was found outside the actinobacteria. The unusual NRPS encoded in SLI 0883 of S. lividans 66 contains a single adenylation domain (A), which predictably recognizes and activates arginine; a phosphopantetheinyl-carrying protein (PCP); and a reductase domain (R). However, it was not possible to identify a condensation domain (C), nor a thioesterase domain (TE) nor any additional adenylation domain inside or in close association with this unusual cluster of biosynthetic genes (defined between genes SLI0 883-SLI0892). The six additional biosynthetic genes predicted, all transcribed in the same direction and potentially transcriptionally coupled, encode alleged enzymes known as confection enzymes while making final structural modifications on a chemical scaffold (FIGS. 6 and 7).

Since SLI0883 and SLI0884 are potentially transcriptionally coupled and only one domain A is bound to the PCP and R dominions, it seems unlikely that a peptide bond can be produced using only SLI0883, by which it was proposed that the homolog of LFT explains the absence of both domains A and C and that in concert with SLI0883 forms a peptide bond. In fact, recent data on the homologous enzyme in E. coli suggest a formation mechanism of peptide bonds similar to the ribosomes and C domains condensation of the NRPSs [25].

To provide a composition of amino acids for the putative product of this pathway, we performed a bioinformatical analysis of the specificity signatures per substrate of the adenylation domain in SLI0883 using well-established prediction tools [26]. The result of this analysis suggested that the adenylation domain is related to arginine. Given the presence of a reductase domain in SLI0883, we predicted that SLI0883 is responsible for the formation of an arginal group, i.e., an aldehyde. Moreover, it is well established that L/F transferase (LFT) is capable of transferring leucines or phenylalanines to basic amino acids, arginine or lysine, forming peptide bonds [27].

Prediction of an N-acetyltransferase SLI0885 enzyme and integration in the biosynthetic pathway SLI0883-4 to produce an N-acylated dipeptide (acyl-phenylalanine/leucine-arginal) with an aldehyde group in its C-terminal, called livipeptin. The following biosynthetic logic was predicted based on the nature of biosynthetic enzymes induced in the group of genes:

It is proposed that the enzymatic product of SLI0884 would form a peptide bond between a leucine or phenylalanine residue, provided by aminoacyl-tRNA, to an arginine residue, united to the PCP of SLI0883 once it has been activated by the adenylation domain of SLI0883. The emerging peptide will be released by the action of reductase (R dominion) on the thioester group, as previously found in myxochelin biosynthesis [28]. A reductive cleavage of the metabolite predicted presumably leads to the release of an aldehydic peptide (FIG. 7). To summarize and as seen in FIG. 7, the analysis of the region where SLI0883-4 are encoded led us to the identification of an N-acyltransferase (SLI0885), an enzyme capable of transferring acyl groups to primary amines. Given the vicinity of these genes, their orientation and reduced intergenic spaces, we predicted that the three genes are transcribed and their products work together for a same biosynthetic pathway, so SLI0885 would add an acyl group to the aldehydic peptide produced by SLI0883-SLI0884.

Based on the predicted functions, we postulate that enzymes encoded by SLI0883-5 are involved in the synthesis of a dipeptide N-acylated (acyl-phenylalanine/leucine arginal) with an aldehyde group at the C-terminal position. This prediction meets the chemical characteristics of the SPAs with protease inhibitory activity, so it is postulated that the natural product result of expression of SLI0883-5 is a SPA with anti-proteolytic activity.

Given the peptidic nature of the metabolites potentially produced by this biosynthesis system of the invention, we denominate Livipeptins to this or these compounds. Therefore, in order to prove the existence of the livipeptins, including their bioactivity and its chemical nature, the following experimental characterization was conducted.

Experimental strategy to identify and characterize the products of the SLI0883-5 route based on obtaining a strain of *S. lividans* 66 Knock-Out lacking the SLI0883-5 genes. For the metabolites identification produced by SLI0883-5, we started from obtaining the Knock-Out mutant lacking these genes; previously reported preliminary data [16] showed that these genes are not expressed in standard growth conditions, so we perform a screening or a phenotype/transcriptional selection to find the optimal conditions for the expression of the biosynthetic pathway; once detected a phenotype associated with the loss of SLI0883-5 we confirm that in these conditions they are transcribed in the wild strain. The construction of SLI0883-5 Knock Out mutant is described in Example 1.

Figure 8:
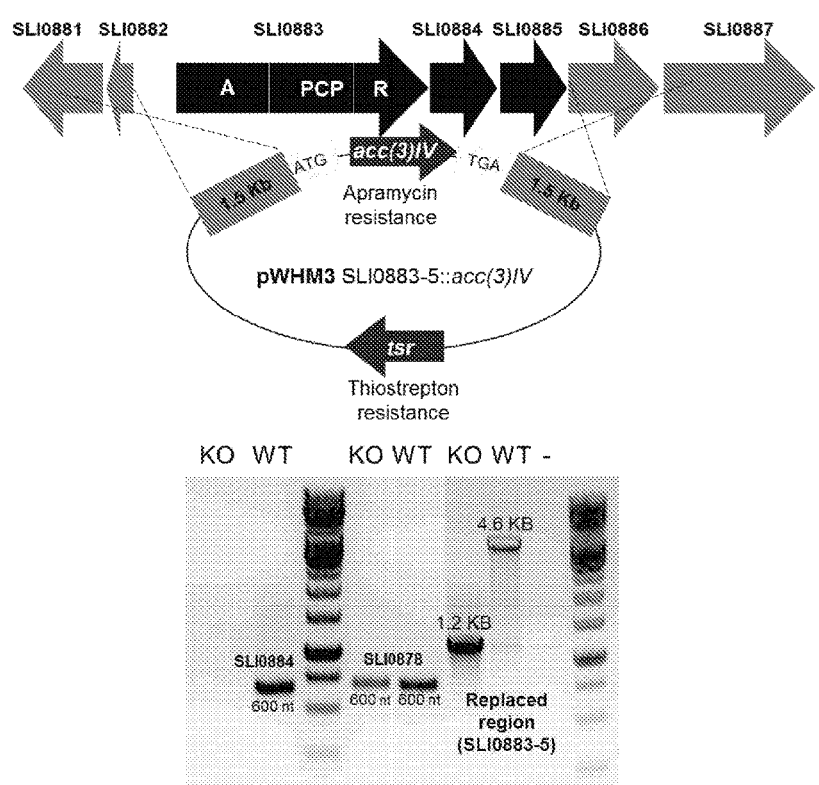
FIG. 8. Shows (left panel) the mutagenesis strategy for deletion of SLI0883-5 with pWHM3_SLI0883-5::acc(3)IV plasmid and (right panel) PCR confirming the mutant genotype (KO) lacking the SLI0883-5 genes.

For obtaining SLI0883-5 mutant, we used a gene replacement method, respecting the reading frame (in frame) by a resistance cassette for apramicyn, which was used as selection marker. The regions corresponding to 1.5 Kb flanking SLI0883-5 were cloned flanking the cassette in pWHM3 plasmid, which contains an additional marker resistant to thiostrepton (FIG. 8). The plasmid pWHM3 is an unstable vector in *Streptomyces*, which is lost after a few rounds of culture of the transformed strain without selection with thiostrepton, making it an excellent vector for mutagenesis [29]. The clones that have undergone the integration of the resistance cassette and the loss of SLI0883-5 by double crossover were selected by resistance to apramycin and thiostrepton sensitivity. The genotype of these clones was confirmed by PCR (FIG. 8) and one of them was selected for further characterization. After integration of this cassette by double crossover, the plasmid was propagated.

We could identify the culture conditions for producing livipeptin by studying delta-SLI0883-5 mutant. In a previous work, we have shown the functional relationship between the mobile genetic element SLP3 of *S. lividans* 66, which is functionally linked to the metal homeostasis [16]. In the same work we have reported that SLI0883-5 genes are not expressed in standard culture conditions [19]. Based on this background, we decided to explore conditions for gene expression using different culture media, emphasizing stress by the addition of metals.

Figure 9:
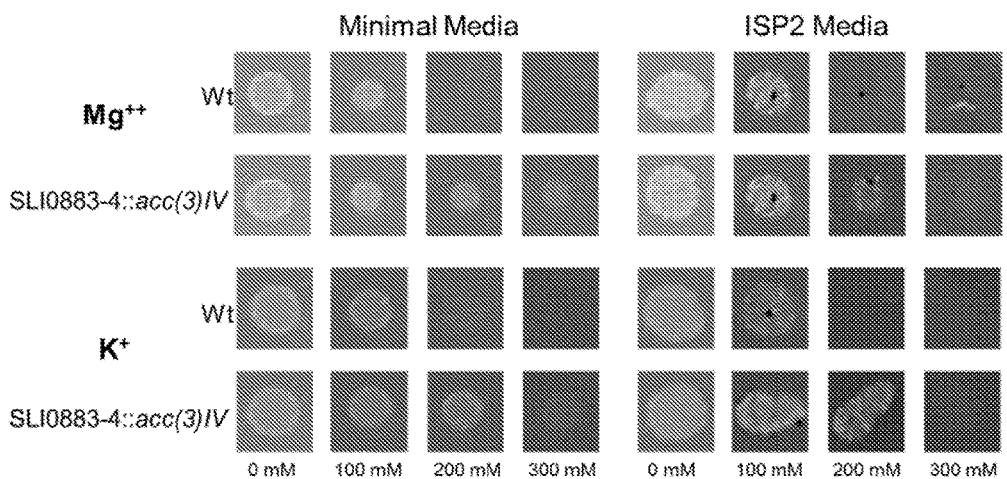
FIG. 9. Shows the response of *S. lividans* 66 to magnesium and potassium. The wild-type (WT) and the mutant delta-SLI883-5 strains were plated on minimal solid medium or in ISP2 medium supplemented with different concentrations of $MgCl_2$ and KCl 200 mM; both metals have a toxic effect on the WT strain, while the mutant strain can grow in 300 mM concentration.

The mutant was grown in solid medium previously chelated to reduce the presence of trace metals. This medium was supplemented with different metals, both transitional and metalloid: Na, Mg, K, Ca, Mn, Fe, Co, Ni, Cu, Zn, and As, in concentrations ranging from 10 µM to 300 mM. The plates were inoculated with fresh spores of *S. lividans* 66 and drops of the mutant containing 10E1 and up to 10E6 spores. After 72 hours of incubation, *S. lividans* 66 did not grow in the presence of 200 mM of KCl and $MgCl_2$, while the mutant did (FIG. 9).

Based on these results, we analyzed the expression of SLI0883-5 by RT-PCR in response to the addition of KCl and $MgCl_2$ in liquid cultures. As shown in FIG. 10, the gene expression is induced by the presence of 300 mM of KCl after four hours, where an identical result was obtained with the use of magnesium at 200 mM. This result implies that the biosynthetic system is active in the presence of $K^{++}$ ions.

Metabolomic and biological-activity analysis of livipeptin. Once found the conditions for the expression of the biosynthetic pathway based on the comparative analysis of the wild strain and the mutant Knock-Out SLI0883-5 in order, we proceeded to perform its metabolic profile by high-performance liquid chromatography (HPLC) coupled to Mass Spectrometry (MS); we proceeded thereafter to the purification of the compounds and simultaneously, to measure their bioactivity by determining the inhibition of the activity of the proteases trypsin and papain. Finally, we carried out a detailed chemical identification of the compounds responsible for these activities by MS/MS analysis, which led to the discovery of molecular species with masses (m/z) characteristic of small peptide aldehydes.

Figure 11:
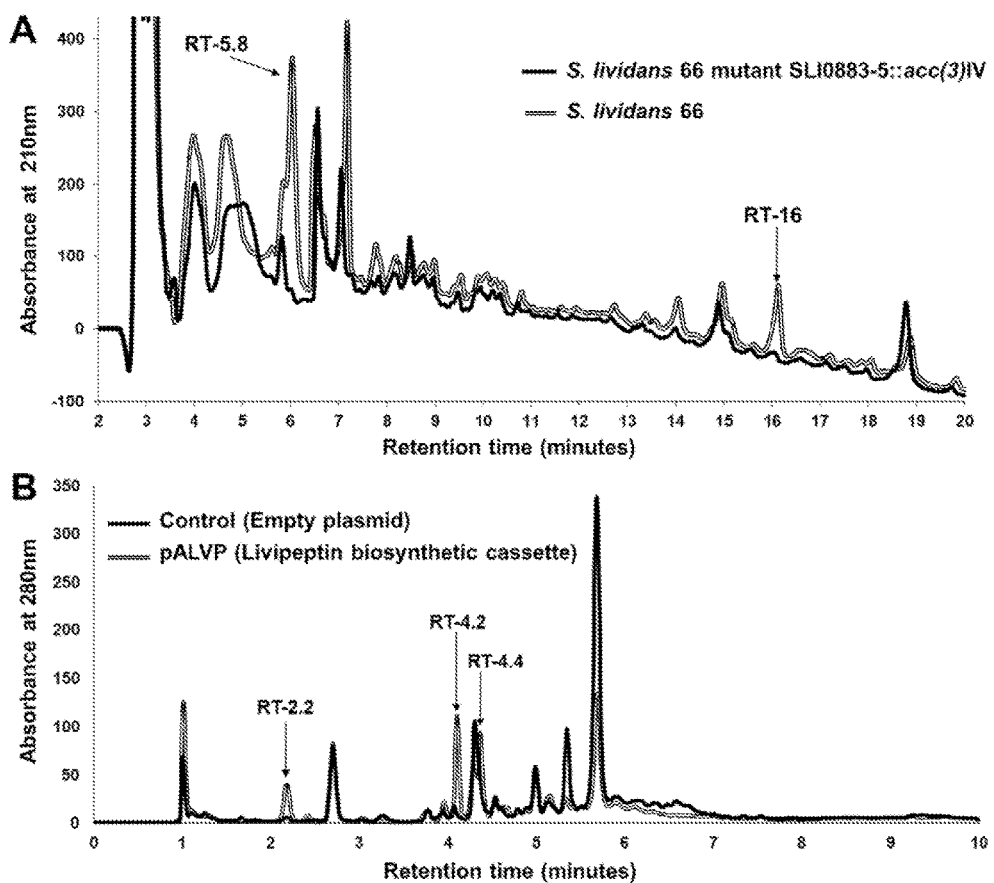
FIG. 11. Shows (A) the metabolic profiles compared by HPLC of the wild strain *S. lividans* 66 and the mutant strain lacking SLI0883-5. The fraction or the peaks corresponding to the retention times of 5.8 minutes (RT5.8) and 16 minutes (RT16) in the chromatogram of the wild strain are absent in the mutant strain; (B) metabolic profiles compared by HPLC of *E. coli* strains transformed with empty pFBG (without insert) and pALVP (pFBG with the lvp biosynthetic cassette). The fractions or peaks corresponding to the retention times 2.2, 4.2 and 4.4 minutes (2.2HET, 4.2 HET and 4.4 HET) in the strain's chromatogram with pALVP are absent in the strain with empty vector.
Figure 12:
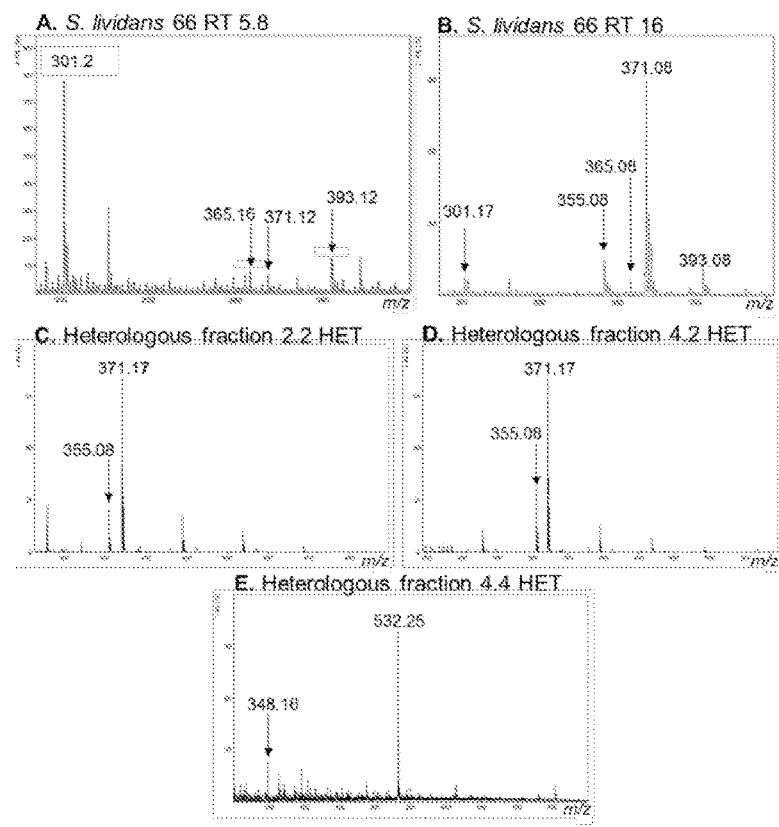
FIG. 12. Shows the MS analysis of (A) RT5.8, (B) RT16, (C) 2.2HET, (D) 4.2HET and (E) 4.4HET, all corresponding to native or heterologous livipeptins.

To determine potential metabolic products of SLI0883-5 genes, we fermented wild and mutant *S. lividans* 66 in R5 medium [33] and induced the gene expression by adding $MgCl_2$ at a concentration of 200 mM. This salt was more practical than the addition of 300 mM of KCl, which at these concentrations is poorly soluble. Aqueous extracts of the fermentation were concentrated 10× and analyzed using HPLC. Comparing the chromatographic profiles of both strains revealed at least two fractions with retention times of 5.8 and 16 minutes (RT5.8 and RT16), absent in the mutant (FIG. 11). These fractions were analyzed using high-resolution mass spectrometry, detecting the mass presence (m/z) consistent with the presence of aldehyde peptides of low molecular weight (FIG. 12). After a MS/MS fragmentation analysis of these masses, we identified masses (m/z) of 365 and 371 as in the RT5.8 fraction as in the RT16 fraction (FIG. 12).

Figure 13:
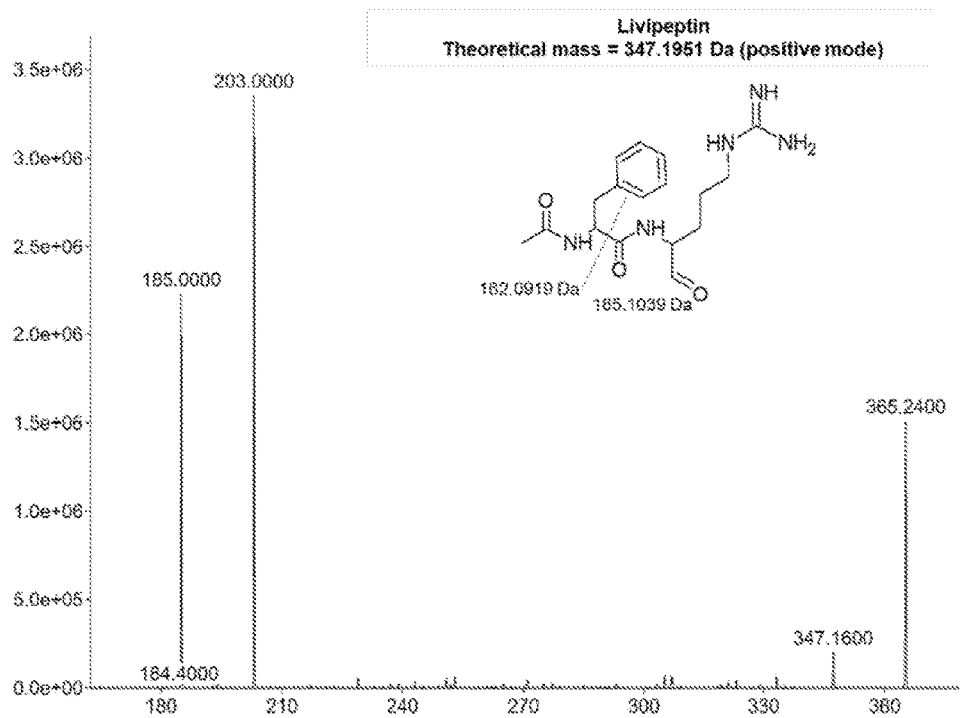
FIG. 13. Shows the MS/MS analysis of the common mass (m/z) 365.24 present in RT5.8 and RT16. This mass is consistent with a small peptide aldehyde from the bacithrocins or thiolstatins family, consistent with acyl-phenylalanine-arginal (formula I).

The structural configuration of the dipeptide corresponding to RT5.8 and RT16 is a dipeptide N-acylated with a C-terminal aldehyde group, specifically acyl-phenylalanine-arginal, whose molecular mass is 347.41 Da. This mass was detected in fractions RT5.8 and RT7 as a hydrated adduct with mass (m/z) of 365.24, which agrees with the structure of bacithrocins/thiolstatins according to an analysis of MS/MS (FIG. 13). These compounds contain Acyl-Leucine-Arginal, and their anti-proteolytic activity has been previously demonstrated (FIG. 2). Because its origin and chemical nature, we decided to call the putative product of this pathway "livipeptin" (formula I) with a general chemical formula of $C_{17}H_{25}N_5O_3$.

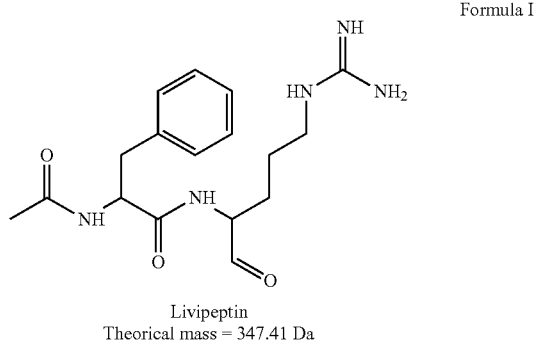 [SMILES: CC(=O)NC(Cc1ccccc1)C(=O)NC(C=O)CCCNC(=N)N]

Formula I

Livipeptin
Theorical mass = 347.41 Da

Figure 14:
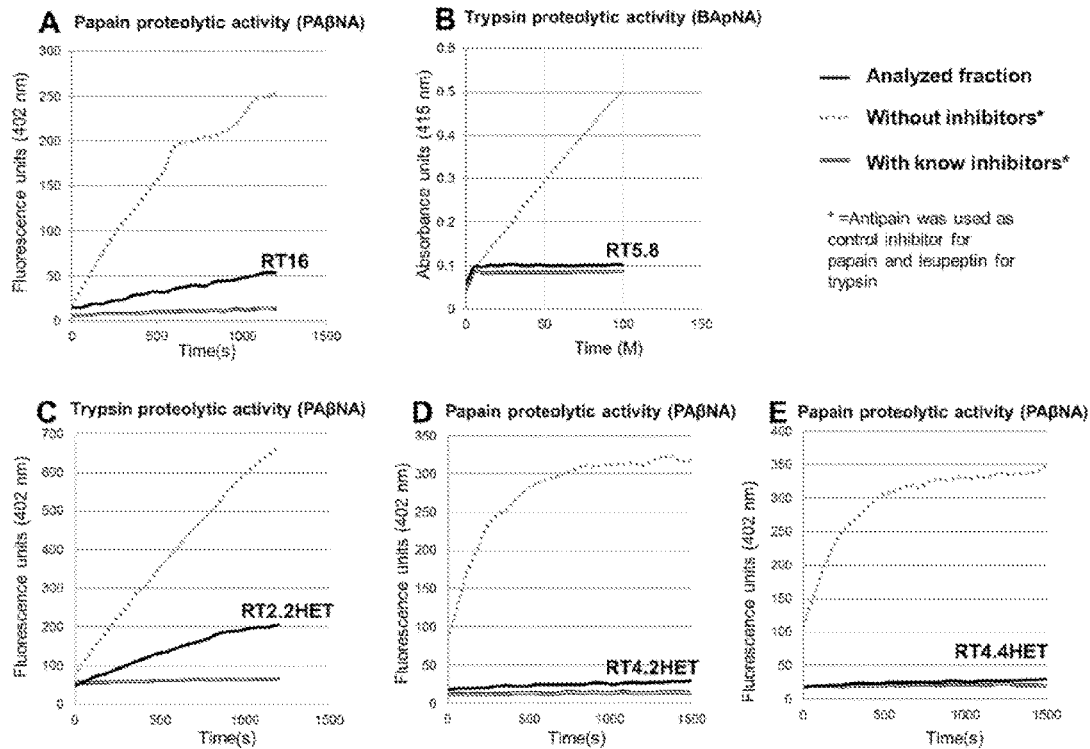
FIG. 14. Shows (A) bioactivity assay of RT16 by means of the inhibition of papain, confirming its anti-proteolytic activity; (B) inhibition assay of proteolytic activity of trypsin by RT5.8, confirming its anti-proteolytic activity. Phenylalanine-Arginine-Naphtylamid (PAβNA) was used for this assay as substrate for proteolysis reaction; (C) inhibition assay of the proteolytic activity of trypsin by RT 2.2HET that confirms its anti-proteolytic capacity against trypsin; (D) inhibition assay of the proteolytic activity of trypsin by RT 2.24HET that confirms its anti-proteolytic capacity against papain; (E) inhibition assay of the proteolytic activity of trypsin by RT 4.4HET that confirms its anti-proteolytic capacity against papain. Benzoyl-DL-Arginine-p-nitroanilide (BApNA) was used in this assay as substrate for proteolysis reaction. Leupeptin and antipain were used as controls or inhibitors.

These fractions were analyzed in vitro using a colorimetric assay wherein Benzoyl-DL-Arginine p-nitroanilide (BApNA), a chromogenic compound, is used as a substrate of various proteases. Owing to their action, the substrate is hydrolyzed obtaining nitroanilide by a colorful reaction, facilitating the detection (or inhibition) of the proteolytic activity in a colorimeter [30]. In this assay, RT5.8 showed inhibitory activity on trypsin. FIG. 14, result of the assay, shows the inhibition of trypsin activity by livipeptin RT5.8, where leupeptin is used as a control. Fractions RT5.8 and RT16 were also analyzed by an enzymatic assay based on fluorimetry. Here, the reaction substrate is phenylalanine-arginine-beta-napthylamide (PAβNA). Hydrolysis of this compound by the action of a protease (trypsin and papain, in our case) releases the naphtylamide group, and the fluorimetric signal of producing this compound is used to measure the proteolytic activity. In FIG. 14, the result of this assay was used as antipapain control to inhibit papain, and leupeptin to inhibit trypsin.

Heterologous expression of livipeptin. This step relates to the genetic manipulation of a bacterial biosynthetic pathway for induction of the biosynthesis and overproduction of livipeptin, and involved the design and construction of a specific biosynthetic genetic system for producing the small peptide aldehyde (SPA) of the present invention with protease inhibitory activity. The gene construct can be expressed in prokaryotic and eukaryotic cell lines so to produce SPAs. Methodological details are described in example 2 to provide the information needed to ensure the reproducibility of the invention. The biosynthetic pathway of the invention is compact, wherein the three genes together add 4.6 Kb, which is ideal for genetic manipulation; in this way, the heterologous expression of the biosynthetic pathway is more feasible. To test this, we constructed a synthetic system of gene expression for producing livipeptin in *Escherichia coli* (FIG. 15), which is commonly used for the expression and purification of heterologous proteins. These experiments demonstrated that *E. coli* strains transformed with *S. lividans* genes are capable of producing livipeptin in situ during the fermentation process (FIGS. 11B, 12, and 14). This biotechnological application can be easily extended to other production systems of heterologous proteins in different cell lines, such as yeast and cell cultures.

Figure 15:
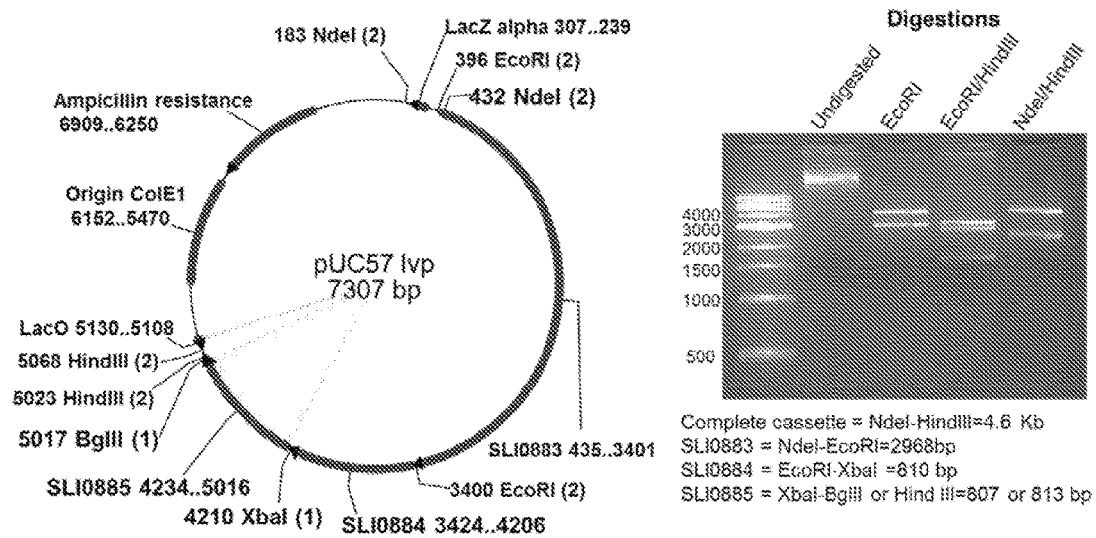
FIG. 15. Shows the biosynthetic cassette of livipeptine (lvp) cloned in pUC57 between the NdeI-HindIII restriction sites (4.6 Kb). Also shows the confirmation of the integrity of the livipeptin biosynthetic cassette through its digestion with different restriction enzymes. The expected size of the digestion fragments is indicated at the bottom.
Figure 16:
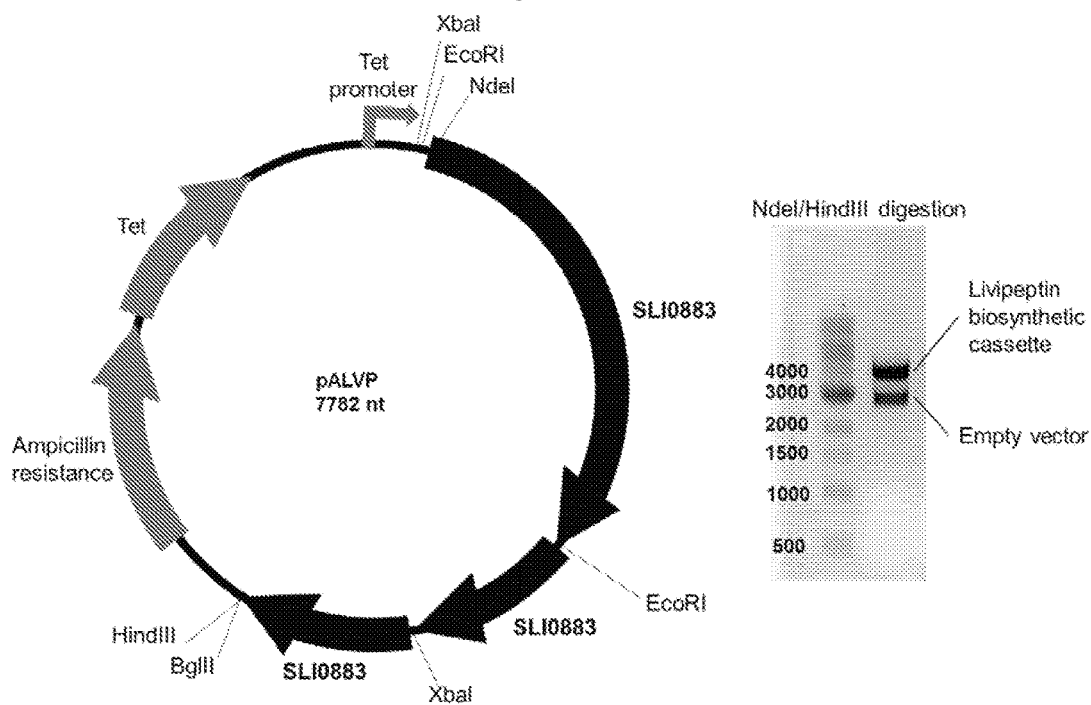
FIG. 16. Shows the genetic map of the pALVP vector for heterologous expression in *E. coli*. Also shows the confirmation of the lvp cassette inducible with anhydrotetracycline, cloned in pFBG (NdeI/HindIII) under the inducible promoter (tet):pALVP, wherein the pALVP vector has a selectable marker of ampicillin resistance.

The sequence of the genes and intergenic regions of SLI0883-5 were obtained from the genome of *Streptomyces lividans* 66 [19]. The design of the gene construct included in silico modification to introduce recognition sequences of various restriction enzymes flanking each gene (FIG. 16). This was done to facilitate the subsequent modification of the biosynthetic pathway for exploration of combinatorial biosynthesis schemes. The vector selected was pFBG, which is a vector with an expression system inducible with tetracycline, which we previously obtained in our laboratory as a derivative from pASK::IBA3plus from IBA GmbH (FIG. 16). The design of the sequence of 4.6 Kbp, including SLI0883-5 (henceforth named the biosynthetic cassette of livipeptin), with restriction sites was synthesized using the services of GenScript, a company dedicated to the synthesis of DNA. The biosynthetic cassette of livipeptin was analyzed by sequencing and endonuclease restriction to confirm the integrity of the sequence (FIG. 15). The vector with the cloned cassette was named pALVP (FIG. 16).

The heterologous expression system of livipeptin in the form of pALVP was introduced into various strains of *E. coli* (FIG. 17) including the cloning host DH5-alfa and the strains for heterologous expression of the proteins Rosetta II, BL21, BL21 star, C41, C43 and C41 with pRIL, a plasmid that helps to express proteins whose codon usage is different from native *E. coli*; C41 pGROEL/ES is a plasmid expressing a system of chaperone proteins that assist in the folding of heterologous proteins; C43 pRIL and C43 pGROEL/ES were also used. The transformed strains with pALVP plasmid and the control plasmid were used for small scale fermentation (150 mL) during 28 hours. The expression system of livipeptin of the present invention was induced at the 4 hours with 40 ng/μL anhydro-tetracycline. The medium used was specially designed to favor de production of livipeptin by adding amino acids that serve as precursors. Cells were separated from the culture by centrifugation, and the supernatant was concentrated 10× for later analysis by HPLC. The HPLC profiles of the strain transformed with pALVP were compared with profiles of strains transformed with the empty plasmid. Thus, we identified the fractions that are only present in the strain with pALVP plasmid and potentially containing heterologous products produced by the introduction of the livipeptin biosynthetic cassette (FIGS. 11B and 12).

Through this analysis, it was determined that the fractions 2.2 HET, 4.2 HET and 4.4 HET are present only in the strain with pALVP (FIGS. 11B and 12). These fractions were analyzed by mass spectrometry and compared to equivalent fractions (with the same retention time) from the strain with empty plasmid. Mass signals over charge m/z=348 (HET4.4), equivalent to the livipeptin obtained as water adduct with a mass of 365, m/z=371 (HET2.2 and HET4.2)

and m/z=532 (HET4.4) that are only present in the mass spectra obtained from differential fractions 2.2, 4.2 and 4.4 HET in the strain with the plasmid pALVP, were considered heterologous products of livipeptin. These products include masses consistent with aldehydic peptides of low molecular weight, consistent with the predicted structure for livipeptin in the present invention (FIG. 11). The anti-proteolytic activity of fractions 2.2, 4.2 and 4.4HET was confirmed through the enzymatic assay described previously, resulting active against papain.

In short, genomic mining, the construction and use of mutants and the use or comparative metabolic profiles of mutant and wild strains have served to demonstrate the link gene-metabolite of the new biosynthetic system described herein, allowing the generation of strains of heterologous expression as proof of concept for the synthesis of a livipeptin SPA, which is unprecedented in the state of the art and has inhibitory activity on proteases.

According to the foregoing, the main objective of the present invention is precisely to provide a system for the biosynthesis of a SPA with inhibitory activity on proteases; additionally, in the present invention, this SPA is characteristic for being a hybrid biosynthesis system: NRPS-tRNA (or NRPS-LFT) unprecedented in the prior art for peptide bond formation, found in *S. lividans* 66.

Derived from this biosynthetic organization, it was found that depending on the conditions, such as medium and expression system, the nature of chemical structures and biological activities varies, opening the possibility to use the system of the present invention to discover new SPAs. Another objective of the invention is to provide a SPA called livipeptin, which is fully characterized by structural elements and a biological activity peculiar to this compound family; we present the experimental bases we used to elucidate their existence and their biosynthesis, and the predicted activity based on the construction of mutants that do not express it.

An embodiment of the invention is the method of biosynthesis for obtaining livipeptin and its use as an inhibitor of proteolysis that occurs in some production processes of proteins of commercial interest; additionally are embodiments of the invention the production processes of proteins of commercial interest known in the prior art, where either livipeptin is added to the process, or the heterologous production in situ of inducible livipeptin is carried out by adding adequate concentrations of metals, both transitional and metalloids; for example, Na, Mg, K, Ca, Mn, Fe, Co, Ni, Cu Zn, and As, their salts including mixtures thereof.

The invention includes the method of obtaining livipeptin by heterologous expression in prokaryotes or eukaryotes, wherein all the essentials elements are provided in the present invention, to realize it, presenting as proof of concept its expression in *E. coli*, using the expression vector pALVP.

Another embodiment of the invention relates to the possibility of exerting a heterologous expression system of proteins of interest with the simultaneous production of protease inhibitors in general and in particular, with the simultaneous production of livipeptin.

When implementing the invention, a person skilled in this technical field will notice the variations, adjustments or implied specifications in methodologies that are within the spirit of the invention; therefore, such variations, adjustments or specifications are within the scope of protection of the present invention.

The following examples are illustrative and are only intended to provide the elements needed to exemplify the invention and do not limit the scope thereof.

EXAMPLE 1

Construction of Livipeptin Mutants in *S. lividans* 66

SLI0883-5::acc(3)IV mutant in *S. lividans* 66 was obtained through double crossover cloning strategy of a mutagenic cassette cloned in pWHM3 [31], as described previously by van Wezel [29]. pWHM3 is a high-copy-number shuttle vector that can replicate in *E. coli* (selected for its resistance to ampicillin) and in a number of *Streptomyces* (selected for its resistance to thiostrepton). However, given its high instability, this plasmid can be cured after a few rounds of non-selective growth transformants strains. Therefore, after loss of the plasmid, only those mutants through a double crossover event have gained a resistance cassette (Apramycin in this case) at the expense of the loss of target genes (here, SLi0883-5) can grow in the presence of the selected antibiotic (FIG. 8).

The mutagenic cassette was constructed using PCR products with 1.5 kilobase pairs upstream and downstream of the codon start of SLI0883 (product 1) and the stop codon of SLI0885 (product 2), respectively. The restriction sites EcoRI-XbaI (product 1) and XbaI-HindIII (product 2) were introduced into the products by the primers. The PCR products were digested with corresponding restriction enzymes, purified, and ligated with pWHM3, previously digested with EcoRI-HindIII in a simultaneous reaction (three-point ligation).

The reaction products of ligation were introduced into *E. coli* DH5alpha competent cells by heat shock. The resulting positive clones were selected with ampicillin and confirmed by PCR and digestion. The apramycin resistance cassette was obtained from pIJ773 [32] after its digestion by XbaI. The released fragment (cassette) was purified and ligated into the plasmid pWHM3 with the products 1 and 2 previously cloned, previously digested with XbaI. The products of the ligation reaction were introduced into DH5alpha competent cells by heat shock and positive clones were selected for resistance to apramycin. The correct construction of the mutagenic plasmid containing the products 1 and 2 flanking the apramycin resistance cassette was confirmed by PCR and digestion.

The mutagenic plasmid in FIG. 8 was introduced into *S. lividans* 66 using protoplast transformation according to the protocols reported by Kieser [33]. Apramycin resistant clones were selected and grown by additional generation and later assess their resistance to thiostrepton, selecting those clones that showed resistance to apramycin (integration of the cassette by double crossover) and sensitivity to thiostrepton (pWHM3 loss, the delivery vector of the cassette). The genotype of the selected mutants was confirmed by PCR. The primers used for this mutagenic process are shown in table 1.

TABLE 1

Primers used for constructing SLI0883-5 in *S. lividans* 66

| Primer | Sequence | Use | SEQ ID NO: |
|---|---|---|---|
| P1_NeoNRP | ctgaggatccgtccccgcacctgggctcc | Product 1 | 1 |
| P2_NeoNRP | gaagttatccatcacctctagagtgtgcgaacgggttcccgga | Product 1 | 2 |
| P3_NeoNRP | gaagttatcgcgcatctctagagtgtgggtcaggcaccgcctc | Product 2 | 3 |
| P4_NeoNRP | ctgaaagcttggcctggtgagctccgagc | Product 2 | 4 |
| NeoNRP_F | gtcacgtcactaagtggcccgg | Confirmation by PCR | 5 |
| NeoNRP_R2 | gtgcggcgaggagttgtattgc | Confirmation by PCR | 6 |

EXAMPLE 2

Design, Synthesis, and Clonation of Livipeptin Biosynthetic Genes

Figure 17:
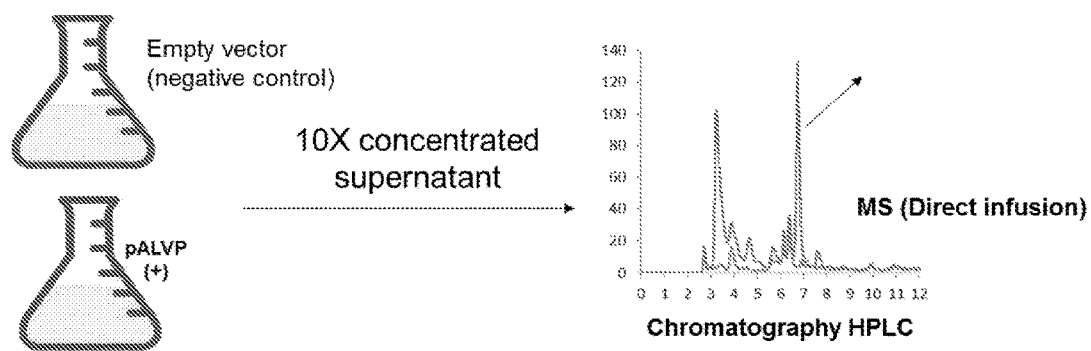
FIG. 17. Shows the experimental strategy for identification of heterologous products of the E. coli/pALVP system.

For the heterologous production of livipeptin in *E. coli*, SLI0883-5 genes were cloned in pFBG, an expression vector for *E. coli*. This vector is regulated by the Tet system; whereby the expression of the inserts is dependent on tetracycline induction. SLI0883-5 were synthesized (GenScript). The original sequence obtained into the genome of *S. lividans* 66 (GenBank Accession: NZ_APVM00000000.1) was modified to introduce restriction sites in the intergenic regions to facilitate the future introduction of other genes to modify the biosynthetic pathway, whereby the synthetic construct was obtained as an insert cloned into the vector pUC57 (FIG. 17). This construct was digested with different combinations of enzymes and the ends of the insert were sequenced to confirm their identity and integrity. To sub-clone the biosynthetic livipeptin cassette, the insert was released from pUC57 by digestion with NdeI and Hindi II enzymes. This insert was purified and ligated to pFBG previously digested with the same enzymes where the ligation products were transformed by heat shock into DHS alpha competent cells; transformants were selected using ampicillin and confirmed by PCR and digestion. The sequence of such construction is shown as SEQ ID NO: 7.

EXAMPLE 3

Microbiological Methods and Culture Media

Spores of *S. lividans* 66 were obtained in SFM medium [33] and the biomass needed for DNA extraction and genomic sequencing was obtained in R5 medium [33]. The following media were used for producing SPA:

Producing medium of livipeptin in *S. lividans* 66: Modified R5 medium (as described in Kieser [33]) without potassium phosphate, containing 0.2 grams of casamino acids per liter and 200 mM $MgCl_2$ dissolved in deionized ultrafiltered water (MilliQ, Millipore).

Heterologous production medium of livipeptin in *E. coli*: M9 Salts (solution 10×: 70 g $Na_2HPO_4.7H_2O$, 30 g $KH_2PO_4$, 5 g NaCl, 10 g $NH_4Cl$) 100 mL/Lt; $MgSO_4$ 1M=2 mL/Lt; $CaCl_2$ 1M=100 μL/Lt dissolved in deionized ultrafiltered water (MilliQ, Millipore). After autoclaving, add glucose 20%=20 mL/Lt and yeast extract=15 mL of solution at 15%. Finally, add 40 ng/mL anhydrotetracycline and 100 μg/mL ampicillin.

EXAMPLE 4

Obtaining Extracts, HPLC-MS and Biological Activity Assays (Inhibition of Proteolytic Activity)

Fermentations were conducted with different strains; supernatants from these fermentations were obtained by centrifugation and were concentrated using a freeze dryer.

Concentrated supernatants (10×) were injected (10 μL) into an HPLC Agilent 1,200 liquid chromatograph with quaternary pump, using a diode array detector at a temperature of 25° C. For separation of sample components, we used a vydac C18 column (4.6 mm i.d.×250 mm). The mobile phase consisted of a mixture of A: TFA 0.1% (trifluoroacetic acid) and B: 100% acetonitrile, wherein the proportions of these solvents varied throughout the chromatographic run according with table 2.

TABLE 2

Chromatographic run conditions

| Time (minutes) | solvent A % | solvent B % |
|---|---|---|
| 0 | 0 | 100 |
| 40 | 65 | 35 |
| 55 | 100 | 0 |

Differential fractions obtained by HPLC, were analyzed by mass spectrometry on LTQ Velos ion trap, Direct injection/ESI (Electrospray ionization), flow: 5 μl/min. For inhibition proteolysis assays, we used fluorometric methods based on the release of naphtylamide group of Phenyl-Arginyl-β-naphtylamide PAβNA, due to the proteolytic action of trypsin and papain. For the inhibition of trypsin by RT5.8, the same principle was used, but here we used a reagent that releases a chromophore (Nalpha-Benzoyl-D,L-arginine 4-nitroanilide or BApNA) whose presence can be detected by a colorimeter [30]. Reaction mixtures for enzymatic assays with PAβNA were prepared as indicated in table 3. The reaction was made in 96-well plates for fluorometer and read on a Tecan fluorometer (excitation wavelength 340 nm and 402 nm emission). For the enzymatic assay using BApNA, the fractions or peaks of interest were dissolved in 100 μL of 0.01M pH 8.0 tris-HCl buffer. For the assay of inhibitory activity, bovine trypsin was used as proteolytic enzyme. Each sample was added 25 μL bovine trypsin, including the enzyme control, which contained buffer instead of the sample. The reaction mixture was added 0.01M pH8 Tris-HCl and incubated at 37° C. for 120 min. Subsequently, the substrate BApNA was added, and the absorbance change was recorded on a colorimeter at 405 nm, every minute for 15 min.

TABLE 3

Reaction mixtures to determine the proteolytic activity of trypsin

|  | Control (−) | Control (+) | Problem sample |
|---|---|---|---|
| Buffer Tris HCl 0.1M pH 8 | 110 µL | 90 µL | 60 µL |
| Trypsin 0.05 mg/mL | 20 µL | 20 µL | 20 µL |
| Leupeptin 0.001 mg/mL | 0 | 20 µL | 0 |
| Problem sample | 0 | 0 | 50 µL |
| Incubate at 37° C. for 15 minutes | | | |
| PAβN 0.1 mg/mL | 20 µL | 20 µL | 20 µL |
| Final volume | 150 µL | 150 µL | 150 µL |

REFERENCES

1. Bachmann B O, et. al. 2014. J Ind Microbiol Biotechnol. 41(2):175-84.
2. Demain A L. 2014. J Ind Microbiol Biotechnol. 41(2): 185-201.
3. Hodgson D A. 2000. Adv Microb Physiol. 2000; 42: 47-238.
4. Moore B S, et. al. 2008. Curr Opin Chem Biol. 12(4): 434-40.
5. Hines J, et. al. 2008 Chem Biol. 15(5):501-12.
6. Kisselev A F, e. at. 2012. Chem Biol. 19(1):99-115.
7. Kaspari M, et. al. 2008. FEBS Lett. 582(5):666-72.
8. Stefanelli S, et. al. 1995. J Antibiot (Tokyo). 48(4): 332-4.
9. Brayer G D, et. al. 1979. Proc Natl Acad Sci USA. 76(1):96-100.
10. Wlodawer A, et. al. 2001. Biochemistry. 40(51):15602-11.
11. Bullock T L, et. al. 1996. J Mol Biol. 255(5):714-25.
12. Kamiyama T., et. al. 1994. The Journal of antibiotics, 47(9), 959-968.
13. Murao, S., et. al. 1985. Agricultural and biological chemistry, 49(3), 895-897.
14. Aoyagi T, et. al. 1969. J Antibiot (Tokyo). 22(6):283-6.
15. Kondo S I, et. al. 1969. Chem Pharm Bull (Tokyo). 17(9):1896-901.
16. Suzukake K, et. al. 1980. J Antibiot (Tokyo). 33(8):857-62.
17. Chen Y, et. al. 2013. J Am Chem Soc. 135(28):10449-56.
18. Weber T, et. al. 2015. Nucleic Acids Res. 43(W1):W237-43.
19. Cruz-Morales P, et al, 2013. Genome Biol Evol. 5(6): 1165-75.
20. Bentley S D, et al. 2002. Nature 417(6885):141-7.
21. Nett M, et. al. 2009. Nat Prod Rep. 26(11):1362-84.
22. Leibowitz M J, et. al. 1969. Biochem Biophys Res Commun. 36(1):47-53.
23. Watanabe K et al. 2007. Nature 449(7164):867-71.
24. Zhang W, et. al. 2011. Proc Natl Acad Sci USA. 108(30):12249-53.
25. Fung A W, et. al. 2011. J Mol Biol. 409(4):617-29.
26. Bachmann B O, et. al. 2009. Methods in Enzymology. 458:181-217.
27. Ichetovkin I E, et. al. 1997. J Biol Chem. 272(52):33009-14.
28. Li Y, et. al. 2008. J Am Chem Soc.; 130(24):7554-5.
29. Van Wezel G P, et al. 2005. Mol Microbiol. 55(2):624-36.
30. Erlanger B F, et. al. 1961. Arch Biochem Biophys. 95:271-8.
31. Vara J, et. al. 1989. J Bacteriol. 171(11):5872-81.
32. Gust B, et. al. 2003. Proc Natl Acad Sci USA. 100(4): 1541-6.
33. Kieser, T, et. al. 2000. Practical *Streptomyces* genetics. Norwich, UK: John Innes Foundation.

The invention claimed is:

1. A method for the heterologous biosynthesis of livipeptin, represented by Formula I:

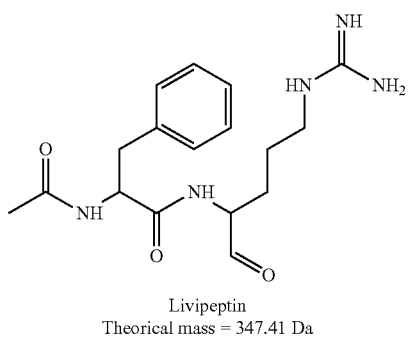

[Formula I]

Livipeptin
Theorical mass = 347.41 Da said method comprising:
  a) culturing a microorganism transformed with an expression vector comprising an lvp cassette comprising SLI0883-SLI0884-SLI0885;
  b) inducing the biosynthesis of livipeptin by adding at least one inductor to the culture containing the transformed microorganism; and
  c) recovering and purifying the fraction of livipeptin from the culture.

2. The method of claim 1, wherein a protein of interest is expressed, and wherein livipeptin exerts an anti-proteolytic activity that favors the expression and yield of said protein of interest within the microorganism.

3. The method of claim 2, wherein the mircoorganism is a prokaryotic or eukaryotic microorganism selected from the group consisting of E. coli DH5alpha, Rosetta II, BL21, BL21 star, C41, C43, and C41 with pRIL; C41 pGROEL/ES, C43 pRIL, and C43 pGROEL/ES.

4. The method of claim 3, wherein the microorganism is E. coli, and wherein the E.coli is transformed with a pALVP expression vector, or derivative thereof.

5. The method of claim 4, wherein the inductor is tetracycline.

6. The method of claim 1, wherein the microorganism is a prokaryotic or eukaryotic microorganism selected from the group consisting of E. coli DH5alpha, Rosetta II, BL21, BL21 star, C41, C43, and C41 with pRIL; C41 pGROEL/ES, C43 pRIL, and C43 pGROEL/ES.

7. The method of claim 6, wherein the prokaryotic microorganism is E. coli, and wherein the E.coli is transformed with a pALVP expression vector, or derivative thereof.

8. The method of claim 7, wherein the inductor is tetracycline.

9. The method of claim 1, wherein proteolysis of proteins of interest is inhibited by the in situ production of livipeptin.

10. The method of claim 9, wherein the protein of interest is recombinantly produced in a eukaryotic or prokaryotic microorganism.

11. The method of claim 1, wherein the vector comprises the nucleic acid sequence comprising SEQ ID NO:7.

12. The method of claim 1, comprising:
a) growing the microoganism-in a culture medium under appropriate conditions for their growth, and
b) adding an inducer selected from the group consisting of a transition metal, a metalloid, a salt of a metalloid, tetracycline, and anhydrotetracycline, or mixtures thereof.

13. The method of claim 12, wherein the metal is selected from at least one of Na, Mg, K, Ca, Mn, Fe, Co, Ni, Cu, Zn, and As or mixtures thereof.

14. The method of claim 1, wherein said lvp cassette has a restriction site in intergenic regions to facilitate the introduction of other genes to alter the biosynthetic pathway.

\* \* \* \* \*

SEQUENCE LISTING

```
<160> NUMBER OF SEQ ID NOS: 9

<210> SEQ ID NO 1
<211> LENGTH: 29
<212> TYPE: DNA
<213> ORGANISM: Artificial sequence
<220> FEATURE:
<221> NAME/KEY: misc_feature
<223> OTHER INFORMATION: Primer P1_NeoNRP

<400> SEQUENCE: 1
ctgaggatcc gtccccgcac ctgggctcc                                    29

<210> SEQ ID NO 2
<211> LENGTH: 43
<212> TYPE: DNA
<213> ORGANISM: Artificial Sequence
<220> FEATURE:
<221> NAME/KEY: misc_feature
<223> OTHER INFORMATION: Primer P2_NeoNRP

<400> SEQUENCE: 2
gaagttatcc atcacctcta gagtgtgcga acgggttccc gga                    43

<210> SEQ ID NO 3
<211> LENGTH: 43
<212> TYPE: DNA
<213> ORGANISM: Artificial Sequence
<220> FEATURE:
<221> NAME/KEY: misc_feature
```

```
<223> OTHER INFORMATION: Primer P3_NeoNRP

<400> SEQUENCE: 3
gaagttatcg cgcatctcta gagtgtgggt caggcaccgc ctc                    43

<210> SEQ ID NO 4
<211> LENGTH: 29
<212> TYPE: DNA
<213> ORGANISM: Artificial Sequence
<220> FEATURE:
<221> NAME/KEY: misc_feature
<223> OTHER INFORMATION: Primer P4_NeoNRP

<400> SEQUENCE: 4
ctgaaagctt ggcctggtga gctccgagc                                   29

<210> SEQ ID NO 5
<211> LENGTH: 22
<212> TYPE: DNA
<213> ORGANISM: Artificial Sequence
<220> FEATURE:
<221> NAME/KEY: misc_feature
<223> OTHER INFORMATION: Primer NeoNRP_F

<400> SEQUENCE: 5
gtcacgtcac taagtggccc gg                                          22

<210> SEQ ID NO 6
<211> LENGTH: 22
<212> TYPE: DNA
<213> ORGANISM: Artificial Sequence
<220> FEATURE:
<221> NAME/KEY: misc_feature
<223> OTHER INFORMATION: Primer NeoNRP_R2

<400> SEQUENCE: 6
gtgcggcgag gagttgtatt gc                                          22

<210> SEQ ID NO 7
<211> LENGTH: 7782
<212> TYPE: DNA
<213> ORGANISM: Artificial sequence
<220> FEATURE:
<221> NAME/KEY: misc_feature
<223> OTHER INFORMATION: cassete lvp SLI0883-SLI0884-SLI0885

<400> SEQUENCE: 7
ccatcgaatg gccagatgat taattcctaa ttttttgttga cactctatca ttgatagagt    60
tattttacca ctccctatca gtgatagaga aaagtgaaat gaatagttcg acaaaaatct   120
agaattcatt ttgtttaact ttaagaaggg gatataccat gggcagcagc catcatcatc   180
atcatcacag cagcggcctg gtgccgcgcg gcagccatat ggagcacgac ggtcgccgca   240
tcgactacac ggaactggat gagcgcgcca accggctcgc gcaccggctc cagagcatgg   300
gagtcatccg cggctccgtg gtcatgacgc acctcgggcg ctccatcgac ctgatcgtgt   360
cattcctggc gaccctcaag gctggggcgg tctatctgcc ggtggagcct ggcgccccgg   420
atgatcggat cgccacttac atcaaggaga cccgctgcac caccgtcgtg acccactcgg   480
atctcgagca ccgcttctcc ggtttcgagg tacggaccgt ctccgtggac ggcagcagcg   540
cgatgacgca cgacagtcgg tcggcctccc gcccgcccga gtcgccgtc ggggctccg    600 acaccgcgta catcgtctac acctcgggct cttcaggcac gccaaggggt gtccaggtca   660
gccattcatc gctcaactac ctgtgccggc acatcaatga ggtgtatggc atcggcccgg   720
```

```
acgatcgggt cctgcagtac gccgcgctgt ccttcgacac ctccatcgag caaatactgg    780
tcgcgctcct caacggagcc acgctcgtgc tgccggagga gctctgggct ccagcgagc    840
tgtccgcccg aattgcctcg ctcggcatct ctgtcatgga cctgacgccg ccgtactggc    900
gcgccttcct ctccgaactc gagcactcgc cgactgagtt accgatccgg ctcacgatcg    960
tcggcggcag tgcggtgcat gccgccgact gccgcacggc gctccgcctg atgccgtact   1020
cccgctcgt caacgcctac gggctcacgg aaacgaccat cacttcgtgc acgatggagg   1080
tcaccccgga gctgcttccc tctgaaggcg ccgcacctat cgggcgcccg ctgccgggca   1140
ctaccgtcct catactcgat caggacatgc ggccggtccc accccagcag gtcggggagc   1200
tgtacatcgg cgggccaggc gtcgcccggg gctatctcgc cgaagaggca tcgaacaagg   1260
accgcttcgt gtcgctggcg acggacgtgg gcggtgcgac gcgcttctat cgcaccggcg   1320
atctgggtcg gtggacagcg gagggaaacc tccacatcac cggacgggcc gaccgccagg   1380
tcaaggtccg tggctaccga gtggagcctg ccgagatcga ggccacgctg tcggcccacc   1440
cgttgatcga cgacgtcgcg gtgaagccgt acagcgtccg ggacgaactg cagctcgccg   1500
cctactacac cgcaagccgc gtccaagctc acttccaatc acgggagtta cgcgacttca   1560
tctctggtcg gctgcccacc ttcatggtcc ccacagcctt cgtccgcctc gacaccatgc   1620
cgacgacggc acacggcaaa cccgatctct ccgcactgcc cgaccggcc cgaggttccg   1680
ccatggggcc agccgcagac cgtgaggctc cggcgaccac cgtggtcgaa cgcgctgtcg   1740
ccggcctgtg gtgccaggtg ctcgacgtcg agtcggttgc acccgacgac aacttcttcg   1800
acctgggcgg cgattcgatc gccgcagccc agttgctctc aaaagtacgg gcctcgctcg   1860
gcatcctgat cacccaggtc cgtccgctca tccggctcct cctcgacgac gcgaccctgc   1920
gcagcttcgc ctctgcggtg gagtcggccc gcgcagggac actcgacacc gccgacgcct   1980
ctcccaccga cttcgcagcc gaagcggctg ttggggtgcc catccagcaa cggcctacga   2040
ccactgactg ggctgaccca gcccacgtgt tcctaaccgg cgcgaccgga ttcctcggaa   2100
tccacctact ccgcgaactc ctcacgacca cgggcgccac ggtgcattgc ctggtccgag   2160
cctcggacac aaaggatgcg aaggagcgca tcacagccaa cgctacgcgc tacctggccg   2220
acccactgga ggagtactgg gccgagggcc ggatcgcgat ggtccccgga gacctgagca   2280
agccccgtct tggcttgacc gaagagagct tcgatcacta cgccgaggtc gtcgacgtga   2340
tccaccaccc gggcgggctg gtcaacttca tctatccgta ctcgcacatg cggcagacga   2400
acgtcgaagg caccgcgcgaa atcattcgac tggccgcccg tcaccggaac attccggtcc   2460
actacgtctc caccatggcg gtcctctcgg gcttcggcac cgccggtacc cggcacgtca   2520
ccgaagacac gccctggcc catgccgacc acctctccgt cgggtacgtg gaaagcaaat   2580
gggtcgccga ggcgctactg cagaacgccg ctgcacaagg cctgccggtc gccatctacc   2640
gcgctgccga catctcaggc gatcggacaa ccggcgcctg gaacaccgcg accgagatgt   2700
gcgcgatgaa gcgcttcatc gtcgacaccg gcacctcgcc gatcgccgag ctccccctgg   2760
actacacgcc agtggaccgc tacgcggccg ctttgctgca catcgccgcc ggccgactgc   2820
ccgcggggga ggtgtaccac ctgaccaacc ccggcaaggt gaacgtcgcg ctcctcgcag   2880
aacgccttcg tgcccgcggc tacacgatcc gcgacgtccc ctgggacgag tggctcgagc   2940
gcatcgtcac cactgccgtg gaagagccgg accaccccat gaccccgttc gcaccgctct   3000
tcatcgatcg gtgctccacc ggcaccatga gcgtcgccga gatgtatctc gagaccacct   3060
```

```
ttcccaccctt ctcccaggac aacgtgacgg ctgccttgcg gggcagcggc atcgagatcc    3120
cgcccgtcga cggcgacatg ctcgaccgct acatcgacta tctgacgtcc atcgacttcc    3180
tgtgaattca ctctccgtga ggtgaacatg atccgaacgc aggatcgagc cgagtccctg    3240
tgggagtcgc tgaatgtcga tgcgggaccg gccgcgcagc ccgtcgctct cggcggcgac    3300
ctcgaacccg cgaccgtcct tgccgcctac cggagcgggc tgtacccgtt tccggtcgac    3360
acggtcgaag ccgcgatcgt caacgaactg acctacgacg ccgatgtcca agccaggcgc    3420
atacatgtcg tccccggcag ggacgacccc ttcaccctgt cctggtggtc tccggatccg    3480
cgcccggtga tccacgtgga ccaggcccgg atccaacgca gcctgcgcca gcagttgcgg    3540
aaccgagcgg actggacgac caccgccgac acctgcttcg cggacgtggt ccgacgctgc    3600
cgggtcggcc gggcccagcg ctggctgacc gacgatctga tgcacagcct gtctcttctg    3660
cacgaacaag gacatgctca cagcgtcgag gtttgggacc gcgatgaact catcggtggc    3720
gtcttcggca tcagggtggg cgccgtcttc agcgcggact cccagttcac gctccgcagc    3780
ggggcaggga agaccgcggt cgccgacctg acacgccgct tcgccgaggc cggcggagtc    3840
gcggtcgacg tccagcgcga gagcgaccac gccaggctcc tcggcgcccg ccccatcccc    3900
aggtcgcact acctcgacct gctggcactc cccaccgccc cacagcccct cgccacgcga    3960
aagctgcccg cgaggcggct caccgagtga tcatctagac aggacccgga gtacaccatg    4020
cctctcacca gcaccgatct gctcgtggtc agcatcgccg agcggccaga ccttgaagaa    4080
gccatgatct cgatggagtc gtcgtggccg gcctacatcc gccccgaccc gctgctcgtg    4140
gactgggcct tcgaccgcca cccggagcac cagctcgtcg tgctcgacga gcaaggtcac    4200
gtcgtcgcac gggcggcggg ggtggggatc gcctgggacg gggatcccgg tcggctgccc    4260
gacgcgggct gggatgcggc actgcggcag tgcctcacag atacgtatgc ggaccggcga    4320
ctcaccgcgc tgtgtgccct ggaaatcgcc gtcgcccccg acaccagtc acggaacctg    4380 tccgcccgta ccctgcgcgc ccttaccgac cacgcccgtc gacacgggtt cctcgatctc    4440
atcggcccgg tccgcccag cctcaagcac gagcgccccg acctgcccat ggccgagtac    4500
atcaagctgc tgcgtgacga cgggctgccc caggacccat ggctccgcat ccatgtcaga    4560
gcgggtggcg aggtcctgaa ggtgtgtccg gcctccatga cgatctccgc tgggctcaac    4620
gaatggcgcg agtggaccgg cctccccctg gacaccagcg gtccgatcac cgtgcccggc    4680
gcactcgccc cagtgaccgt cagcctcgag cacgactacg cggtgtacgt cgaacccaac    4740
gtgtgggtca ggcaccgcct caccgacaag cgccccaccg acaaggagaa ctccgtatga    4800
agatctaagc ttgacctgtg aagtgaaaaa tggcgcacat tgtgcgacat ttttttttgtc    4860 tgccgtttac cgctactgcg tcacggatct ccacgcgccc tgtagcggcg cattaagcgc    4920
ggcgggtgtg gtggttacgc gcagcgtgac cgctacactt gccagcgccc tagcgcccgc    4980
tcctttcgct ttcttccctt cctttctcgc cacgttcgcc ggctttcccc gtcaagctct    5040
aaatcggggg ctcccttag ggttccgatt tagtgcttta cggcacctcg accccaaaaa    5100
acttgattag ggtgatggtt cacgtagtgg gccatcgccc tgatagacgg ttttcgccc    5160 tttgacgttg gagtccacgt tctttaatag tggactcttg ttccaaactg gaacaacact    5220
caaccctatc tcggtctatt cttttgattt ataagggatt ttgccgattt cggcctattg    5280
gttaaaaaat gagctgattt aacaaaaatt taacgcgaat tttaacaaaa tattaacgct    5340
tacaatttca ggtggcactt ttcggggaaa tgtgcgcgga ccccctattt gtttattttt    5400
ctaaatacat tcaaatatgt atccgctcat gagacaataa ccctgataaa tgcttcaata    5460
```

-continued

```
atattgaaaa aggaagagta tgagtattca acatttccgt gtcgcccta ttcccttttt      5520 tgcggcattt tgccttcctg tttttgctca cccagaaacg ctggtgaaag taaaagatgc     5580
tgaagatcag ttgggtgcac gagtgggtta catcgaactg gatctcaaca gcggtaagat     5640
ccttgagagt tttcgccccg aagaacgttt tccaatgatg agcacttta aagttctgct     5700 atgtggcgcg gtattatccc gtattgacgc cgggcaagag caactcggtc gccgcataca    5760
ctattctcag aatgacttgg ttgagtactc accagtcaca gaaaagcatc ttacggatgg     5820
catgacagta agagaattat gcagtgctgc cataaccatg agtgataaca ctgcggccaa     5880
cttacttctg acaacgatcg gaggaccgaa ggagctaacc gcttttttgc acaacatggg     5940
ggatcatgta actcgccttg atcgttggga accggagctg aatgaagcca taccaaacga    6000
cgagcgtgac accacgatgc ctgtagcaat ggcaacaacg ttgcgcaaac tattaactgg    6060
cgaactactt actctagctt cccggcaaca attgatagac tggatggagg cggataaagt    6120
tgcaggacca cttctgcgct cggcccttcc ggctggctgg tttattgctg ataaatctgg    6180
agccggtgag cgtggctctc gcggtatcat tgcagcactg gggccagatg gtaagccctc    6240
ccgtatcgta gttatctaca cgacggggag tcaggcaact atggatgaac gaaatagaca    6300
gatcgctgag ataggtgcct cactgattaa gcattggtag gaattaatga tgtctcgttt    6360
agataaaagt aaagtgatta acagcgcatt agagctgctt aatgaggtcg gaatcgaagg    6420
tttaacaacc cgtaaactcg cccagaagct aggtgtagag cagcctacat tgtattggca    6480
tgtaaaaaat aagcgggctt tgctcgacgc cttagccatt gagatgttag ataggcacca    6540
tactcacttt tgccctttag aaggggaaag ctggcaagat ttttttacgta ataacgctaa    6600 aagttttaga tgtgctttac taagtcatcg cgatggagca aaagtacatt taggtacacg    6660
gcctacagaa aaacagtatg aaactctcga aaatcaatta gccttttat gccaacaagg     6720 tttttcacta gagaatgcat tatatgcact cagcgcagtg gggcattta ctttaggttg     6780 cgtattggaa gatcaagagc atcaagtcgc taaagaagaa agggaaacac ctactactga    6840
tagtatgccg ccattattac gacaagctat cgaattattt gatcaccaag gtgcagagcc    6900
agccttctta ttcggccttg aattgatctt atgcggatta gaaaaacaac ttaaatgtga    6960
aagtgggtct taaaagcagc ataacctttt tccgtgatgg taacttcact agtttaaaag    7020
gatctaggtg aagatccttt ttgataatct catgaccaaa atcccttaac gtgagttttc     7080
gttccactga gcgtcagacc ccgtagaaaa gatcaaagga tcttcttgag atcctttttt    7140
tctgcgcgta atctgctgct tgcaaacaaa aaaaccaccg ctaccagcgg tggtttgttt    7200
gccggatcaa gagctaccaa ctctttttcc gaaggtaact ggcttcagca gagcgcagat    7260
accaaatact gtccttctag tgtagccgta gttaggccac cacttcaaga actctgtagc    7320
accgcctaca tacctcgctc tgctaatcct gttaccagtg ctgctgcca gtggcgataa     7380 gtcgtgtctt accgggttgg actcaagacg atagttaccg gataaggcgc agcggtcggg    7440
ctgaacgggg ggttcgtgca cacagcccag cttggagcga acgacctaca ccgaactgag    7500
atacctacag cgtgagctat gagaaagcgc cacgcttccc gaagggagaa aggcggacag    7560
gtatccggta agcggcaggg tcggaacagg agagcgcacg agggagcttc caggggggaaa   7620 cgcctggtat ctttatagtc ctgtcgggtt tcgccacctc tgacttgagc gtcgattttt    7680
gtgatgctcg tcaggggggc ggagcctatg gaaaaacgcc agcaacgcgg ccttttacg     7740 gttcctggcc ttttgctggc cttttgctca catgacccga ca                       7782
```

```
<210> SEQ ID NO 8
<211> LENGTH: 6
<212> TYPE: PRT
<213> ORGANISM: Streptomyces sp.
<300> PUBLICATION INFORMATION:
<301> AUTHORS: Chen Y, McClure RA, Zheng Y, Thomson RJ, Kelleher NL
<302> TITLE: Proteomics guided discovery of flavopeptins: anti-
      proliferative aldehydes synthesized by a reductase domain-
      containing non-ribosomal peptide synthetase
<303> JOURNAL: J Am Chem Soc
<304> VOLUME: 135
<305> ISSUE: 28
<306> PAGES: 10449-10456
<307> DATE: 2013-07-17
<313> RELEVANT RESIDUES IN SEQ ID NO: (1)..(6)

<400> SEQUENCE: 8

Ile Gln Ile Gln Val Phe
1               5

<210> SEQ ID NO 9
<211> LENGTH: 6
<212> TYPE: PRT
<213> ORGANISM: Streptomyces sp.
<300> PUBLICATION INFORMATION:
<301> AUTHORS: Chen Y, McClure RA, Zheng Y, Thomson RJ, Kelleher NL
<302> TITLE: Proteomics guided discovery of flavopeptins: anti-
      proliferative aldehydes synthesized by a reductase domain-
      containing non-ribosomal peptide synthetase
<303> JOURNAL: J Am Chem Soc
<304> VOLUME: 135
<305> ISSUE: 28
<306> PAGES: 10449-10456
<307> DATE: 2013-07-17
<313> RELEVANT RESIDUES IN SEQ ID NO: (1)..(6)

<400> SEQUENCE: 9

Ile Gln Ile Gln Ile Phe
1               5
```